United States Patent
Kleuskens et al.

(10) Patent No.: US 11,730,636 B2
(45) Date of Patent: Aug. 22, 2023

(54) ABSORBENT ARTICLE WITH BODYSIDE LINER PROVIDING A BARRIER REGION

(71) Applicant: Kimberly-Clark Worldwide, Inc., Neenah, WI (US)

(72) Inventors: Sarah A. Kleuskens, Neenah, WI (US); SangWook Lee, Setagayaku (JP)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 885 days.

(21) Appl. No.: 16/632,756

(22) PCT Filed: Jul. 31, 2017

(86) PCT No.: PCT/US2017/044567
§ 371 (c)(1),
(2) Date: Jan. 21, 2020

(87) PCT Pub. No.: WO2019/027406
PCT Pub. Date: Feb. 7, 2019

(65) Prior Publication Data
US 2020/0155372 A1 May 21, 2020

(51) Int. Cl.
*A61F 13/49* (2006.01)
*A61F 13/494* (2006.01)
(Continued)

(52) U.S. Cl.
CPC ........ *A61F 13/4942* (2013.01); *A61F 13/496* (2013.01); *A61F 13/49413* (2013.01);
(Continued)

(58) Field of Classification Search
CPC .......... A61F 13/49017; A61F 13/49406; A61F 13/49413; A61F 13/4942; A61F 13/537;
(Continued)

(56) References Cited

U.S. PATENT DOCUMENTS

| 4,753,646 A | 6/1988 | Enloe |
| 5,269,775 A | 12/1993 | Freeland et al. |

(Continued)

FOREIGN PATENT DOCUMENTS

| CN | 1143904 A | 2/1997 |
| CN | 1235012 A | 11/1999 |

(Continued)

*Primary Examiner* — Catharine L Anderson
(74) *Attorney, Agent, or Firm* — Kimberly-Clark Worldwide, Inc.

(57) ABSTRACT

An absorbent article can include a bodyside liner that provides a barrier region. The barrier region can be a central portion of the bodyside liner not coupled to the absorbent body. The barrier region can include a first longitudinal side edge and a second longitudinal side edge. The first longitudinal side edge can be coupled to the projection portion of the first containment flap. The second longitudinal side edge can be coupled to the projection portion of the second containment flap. When the absorbent article is in the relaxed configuration and the projection portion of the first containment flap and the projection portion of the second containment flap extend away from the absorbent body, the central portion of the bodyside liner extends away from absorbent body.

20 Claims, 12 Drawing Sheets

(51) Int. Cl.
   *A61F 13/496* (2006.01)
   *A61F 13/511* (2006.01)
   *A61F 13/514* (2006.01)
   *A61F 13/537* (2006.01)
   *A61F 13/15* (2006.01)

(52) U.S. Cl.
   CPC ........ *A61F 13/514* (2013.01); *A61F 13/5116* (2013.01); *A61F 13/53713* (2013.01); *A61F 2013/1591* (2013.01); *A61F 2013/49092* (2013.01)

(58) Field of Classification Search
   CPC ...... A61F 13/53747; A61F 2013/49088; A61F 2013/49092; A61F 2013/49433; A61F 13/495; A61F 13/4956
   See application file for complete search history.

(56) References Cited

U.S. PATENT DOCUMENTS

| | | | |
|---|---|---|---|
| 5,531,730 | A | 7/1996 | Dreier |
| 5,576,091 | A | 11/1996 | Zajaczkowski et al. |
| 5,766,411 | A | 6/1998 | Wilson |
| 5,810,799 | A | 9/1998 | Slater |
| 5,938,652 | A | 8/1999 | Sauer |
| 5,968,028 | A | 10/1999 | Roe et al. |
| 6,010,490 | A | 1/2000 | Freeland et al. |
| 6,315,764 | B1 | 11/2001 | Faulks et al. |
| 6,450,998 | B1 | 9/2002 | Otsubo et al. |
| 6,685,689 | B1 | 2/2004 | Rönnberg |
| 6,699,228 | B1 | 3/2004 | Chmielewski et al. |
| 6,749,593 | B1 | 6/2004 | Flohr et al. |
| 6,786,895 | B1 | 9/2004 | Schmitz |
| 6,896,668 | B2 | 5/2005 | Kashiwagi et al. |
| 6,921,394 | B2 | 7/2005 | Sayama et al. |
| 7,037,298 | B2 | 5/2006 | Ohshima et al. |
| 7,252,657 | B2 | 8/2007 | Mishima et al. |
| 7,470,264 | B2 | 12/2008 | Mishima et al. |
| 7,563,257 | B2 | 7/2009 | Nakajima et al. |
| 7,666,173 | B2 | 2/2010 | Mishima et al. |
| 7,722,587 | B2 | 5/2010 | Suzuki et al. |
| 7,755,888 | B2 | 7/2010 | Sun |
| 7,763,002 | B2 | 7/2010 | Otsubo |
| 7,766,888 | B2 | 8/2010 | Mishima et al. |
| 7,812,213 | B2 | 10/2010 | Doverbo et al. |
| 7,867,210 | B2 | 1/2011 | Mori et al. |
| 8,016,803 | B2 | 9/2011 | Mueller et al. |
| 8,029,486 | B2 | 10/2011 | Nakajima et al. |
| 8,157,778 | B2 | 4/2012 | Moriya et al. |
| 8,197,457 | B2 * | 6/2012 | Suzuki ............. A61F 13/495 604/385.27 |
| 8,246,595 | B2 | 8/2012 | Carlson et al. |
| 8,298,204 | B2 | 10/2012 | Otsubo |
| 8,377,025 | B2 | 2/2013 | Nakajima et al. |
| 8,679,084 | B2 | 3/2014 | Kurihara |
| 8,728,050 | B2 | 5/2014 | Nitta et al. |
| 8,889,946 | B2 | 11/2014 | Hermansson et al. |
| 9,050,218 | B2 | 6/2015 | Martynus et al. |
| 9,050,219 | B2 | 6/2015 | Martynus et al. |
| 9,084,698 | B2 * | 7/2015 | Ichikawa .......... A61F 13/53409 |
| 9,314,382 | B2 | 4/2016 | Zilm |
| 9,456,935 | B2 | 10/2016 | Greening, II et al. |
| 2003/0045853 | A1 | 3/2003 | Sauer |
| 2003/0083631 | A1 | 5/2003 | Chen et al. |
| 2004/0116883 | A1 | 6/2004 | Krautkramer et al. |
| 2005/0228358 | A1 | 10/2005 | Mishima et al. |
| 2006/0184151 | A1 | 8/2006 | Onishi et al. |
| 2006/0271005 | A1 | 11/2006 | LaVon et al. |
| 2006/0287635 | A1 | 12/2006 | Angel |
| 2010/0274209 | A1 | 10/2010 | Roe et al. |
| 2011/0106040 | A1 | 5/2011 | Minato et al. |
| 2012/0022489 | A1 | 1/2012 | Wakasugi et al. |
| 2012/0040039 | A1 | 2/2012 | Alkmin et al. |
| 2013/0012898 | A1 | 1/2013 | Bergendahl et al. |
| 2014/0221955 | A1 | 8/2014 | Brown et al. |
| 2014/0296809 | A1 | 10/2014 | Hammons et al. |
| 2015/0032071 | A1 | 1/2015 | Suzuki et al. |
| 2015/0045759 | A1 | 2/2015 | Martynus et al. |
| 2015/0057631 | A1 | 2/2015 | Dieringer et al. |
| 2015/0164706 | A1 | 6/2015 | Ben-Natan et al. |
| 2015/0209195 | A1 | 7/2015 | Martynus et al. |
| 2015/0223995 | A1 | 8/2015 | Martynus et al. |
| 2015/0223996 | A1 | 8/2015 | Martynus et al. |
| 2015/0257946 | A1 | 9/2015 | Martynus et al. |
| 2016/0256332 | A1 | 9/2016 | Brown et al. |
| 2016/0256333 | A1 | 9/2016 | Brown et al. |
| 2016/0278994 | A1 | 9/2016 | Martynus et al. |
| 2019/0380885 | A1 | 12/2019 | Enz et al. |
| 2020/0022848 | A1 | 1/2020 | Enz et al. |

FOREIGN PATENT DOCUMENTS

| | | | |
|---|---|---|---|
| CN | 1372874 | A | 10/2002 |
| CN | 1539391 | A | 10/2004 |
| CN | 1572267 | A | 2/2005 |
| CN | 104822352 | A | 8/2015 |
| EP | 0091412 | B1 | 5/1987 |
| JP | 3186261 | A | 8/1991 |
| JP | 8196565 | A | 8/1996 |
| JP | 2003144488 | A | 5/2003 |
| KR | 20020062695 | A | 7/2002 |
| KR | 20070013398 | A | 1/2007 |
| WO | 9963921 | A1 | 12/1999 |
| WO | 0106974 | A1 | 2/2001 |
| WO | 15005166 | A1 | 1/2015 |
| WO | 15055695 | A1 | 4/2015 |
| WO | 15055696 | A1 | 4/2015 |
| WO | 15198928 | A1 | 12/2015 |
| WO | 15198929 | A1 | 12/2015 |
| WO | 16159978 | A1 | 10/2016 |
| WO | 18143921 | A1 | 8/2018 |

* cited by examiner

ABSORBENT ARTICLE WITH BODYSIDE LINER PROVIDING A BARRIER REGION

TECHNICAL FIELD

The present disclosure relates to absorbent articles.

BACKGROUND OF THE DISCLOSURE

A primary function of personal care absorbent articles is to absorb and retain body exudates such as urine, fecal material, blood, and menses with additional desired attributes including low leakage of the exudates from the absorbent article and a dry feel to the wearer of the absorbent article. By preventing leakage of the exudates from the absorbent article, the absorbent article intends to prevent the body exudates from soiling or contaminating a wearer's or caregiver's clothing or other articles, such as bedding, that can come in contact with the wearer.

One common mode of failure is for exudates to leak out of the rear waist region or the front waist region of an absorbent article. Movement of exudates within the absorbent article against a wearer's skin can also be problematic in causing more difficult cleaning of the wearer's skin and additional opportunity for irritation to the wearer's skin. This may be more common of an occurrence for semi-solid fecal material, such as low viscosity fecal material, which can be prevalent with younger children. Such exudates can move around on the bodyside liner of an absorbent article under the influence of gravity, motion, force, and pressure by the wearer of the absorbent article. If the fecal material that is not absorbed or contained by the absorbent article does leak from the absorbent article, not only does the wearer's absorbent article need to be changed, but the wearer's clothing and/or bedding often also needs to be changed, resulting in additional work, expense, and stress for the caregiver.

Attempts have been made in the past to provide containment systems, however, such systems can be complex to manufacture and/or require additional materials to be added to the absorbent article, adding cost to the manufacturing process and/or to the absorbent article. Further, some containment system have not functioned adequately at preventing exudates that are not absorbed from moving on the bodyside liner to other locations within the absorbent article.

Thus, there is a desire for improvements to absorbent articles that include systems to prevent the spreading of exudates and prevent the leakage of exudates from the absorbent article.

SUMMARY OF THE DISCLOSURE

In one embodiment, an absorbent article can include a front waist region, a rear waist region, a crotch region, a longitudinal axis, and a lateral axis. The absorbent article can include a chassis including a bodyside liner, an outer cover, and an absorbent body. The absorbent body can be disposed between the bodyside liner and the outer cover. The bodyside liner can include a length that is at least 50% of a length of the absorbent article as measured in a direction parallel to the longitudinal axis. The absorbent article can also include a pair of containment flaps including a first containment flap and a second containment flap. The first containment flap and the second containment flap can each extend from the front waist region to the second waist region. The pair of containment flaps can each include a base portion coupled to the chassis and a projection portion extending away from the absorbent body when the absorbent article is in a relaxed configuration. The bodyside liner includes a central barrier region in the crotch region. The central barrier region can be a central portion of the bodyside liner not coupled to the absorbent body. The central barrier region can include a first longitudinal side edge and a second longitudinal side edge. The first longitudinal side edge can be coupled to the projection portion of the first containment flap and the second longitudinal side edge can be coupled to the projection portion of the second containment flap such that when the absorbent article is in the relaxed configuration and the projection portion of the first containment flap and the projection portion of the second containment flap extend away from the absorbent body, the central portion of the bodyside liner extends away from the absorbent body.

In another embodiment, an absorbent article can include a front waist region, a rear waist region, a crotch region, a longitudinal axis and a lateral axis. The absorbent article can include a chassis including a bodyside liner, an outer cover, and an absorbent body. The absorbent body can be disposed between the bodyside liner and the outer cover. The bodyside liner can include a length that is at least 50% of a length of the absorbent article as measured in a direction parallel to the longitudinal axis. The absorbent article can also include a pair of containment flaps including a first containment flap and a second containment flap. The first containment flap and the second containment flap can each extend from the front waist region to the second waist region. The pair of containment flaps can each include a base portion coupled to the chassis and a projection portion extending away from the absorbent body when the absorbent article is in a relaxed configuration. The bodyside liner can include a barrier region. The barrier region can be a portion of the bodyside liner configured to move independently from the absorbent body and to extend away from the absorbent body when the absorbent article is in the relaxed configuration.

In yet another embodiment, an absorbent article can include a front waist region, a rear waist region, a crotch region, a longitudinal axis and a lateral axis. The absorbent article can include a chassis including a bodyside liner, an outer cover, and an absorbent body. The absorbent body can be disposed between the bodyside liner and the outer cover. The bodyside liner can include a length that is at least 50% of a length of the absorbent article as measured in a direction parallel to the longitudinal axis. The absorbent article can also include a pair of containment flaps including a first containment flap and a second containment flap. The first containment flap and the second containment flap can each extend from the front waist region to the second waist region. The pair of containment flaps can each include a base portion coupled to the chassis and a projection portion extending away from the absorbent body when the absorbent article is in a relaxed configuration. The absorbent article can also include a flap connector. The flap connector can include a first end region, a middle portion, and a second end region. The first end region of the flap connector can be coupled to the projection portion of the first containment flap. The second end region of the flap connector can be coupled to the projection portion of the second containment flap. The bodyside liner can include a barrier region in the crotch region of the absorbent article. The barrier region can be a portion of the bodyside liner not coupled to the absorbent body and can include a first longitudinal side edge and a second longitudinal side edge. The barrier region can be coupled to the middle portion of the flap connector. The flap connector and the barrier region can be configured such that when the absorbent article is in the relaxed configuration and the projection portion of the first containment flap and the projection portion of the second containment flap extend away from the absorbent body, the flap connector and the portion of the bodyside liner not coupled to the absorbent body extend away from the absorbent body.

BRIEF DESCRIPTION OF DRAWINGS

A full and enabling disclosure thereof, directed to one of ordinary skill in the art, is set forth more particularly in the remainder of the specification, which makes reference to the appended figures in which.

Figure 1:
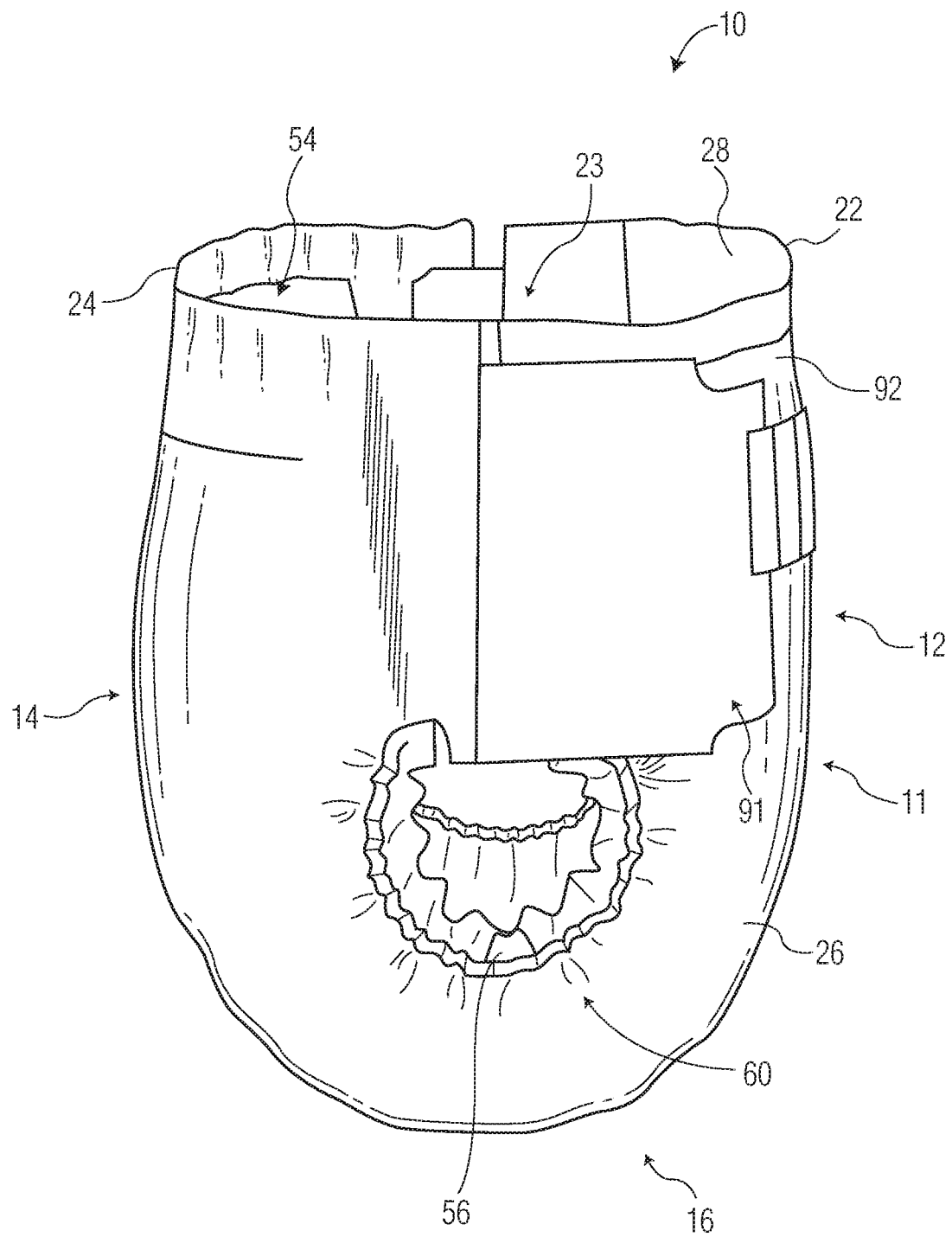
FIG. 1 is side perspective view of an exemplary embodiment of an absorbent article, such as a diaper, in a fastened condition.

Repeat use of reference characters in the present specification and drawings is intended to represent the same or analogous features or elements of the disclosure.

DETAILED DESCRIPTION OF THE DISCLOSURE

In an embodiment, the present disclosure is generally directed towards an absorbent article 10, 110, 210, 310 having a bodyside liner 28 configured to provide a barrier region 56 that provides a barrier for body exudates. Each example is provided by way of explanation and is not meant as a limitation. For example, features illustrated or described as part of one embodiment or figure can be used on another embodiment or figure to yield yet another embodiment. It is intended that the present disclosure include such modifications and variations.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Definitions

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, feminine hygiene products, including, but not limited to, menstrual pads or pants, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" or "coupled" refers herein to the joining, adhering, connecting, attaching, or the like, of two elements. Two elements will be considered bonded or coupled together when they are joined, adhered, connected, attached, or the like, directly to one another or indirectly to one another, such as when each is directly bonded to intermediate elements. The bonding or coupling of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

The term "user" or "caregiver" refers herein to one who fits an absorbent article, such as, but not limited to, a diaper, diaper pant, training pant, youth pant, incontinent product, or other absorbent article about the wearer of one of these absorbent articles. A user and a wearer can be one and the same person.

Absorbent Article:

Referring to FIGS. 1-4C, a non-limiting illustration of an absorbent article 10, for example, a diaper, is illustrated. FIGS. 5-8 also illustrate alternative embodiments of absorbent articles 110, 210, 310 with similar configurations and components to the absorbent article 10 of FIGS. 1-4C unless otherwise noted. Other embodiments of the absorbent article could include training pants, youth pants, adult incontinence garments, and feminine hygiene articles. While the embodiments and illustrations described herein may generally apply to absorbent articles manufactured in the product longitudinal direction, which is hereinafter called the machine direction manufacturing of a product, it should be noted that one of ordinary skill in the art could apply the information herein to absorbent articles manufactured in the latitudinal direction of the product, which hereinafter is called the cross direction manufacturing of a product, without departing from the spirit and scope of the disclosure. For example, the absorbent article 410 in FIGS. 9 and 10 provides an exemplary embodiment of an absorbent article 410 that can be manufactured in cross-direction manufacturing process.

Figure 2:
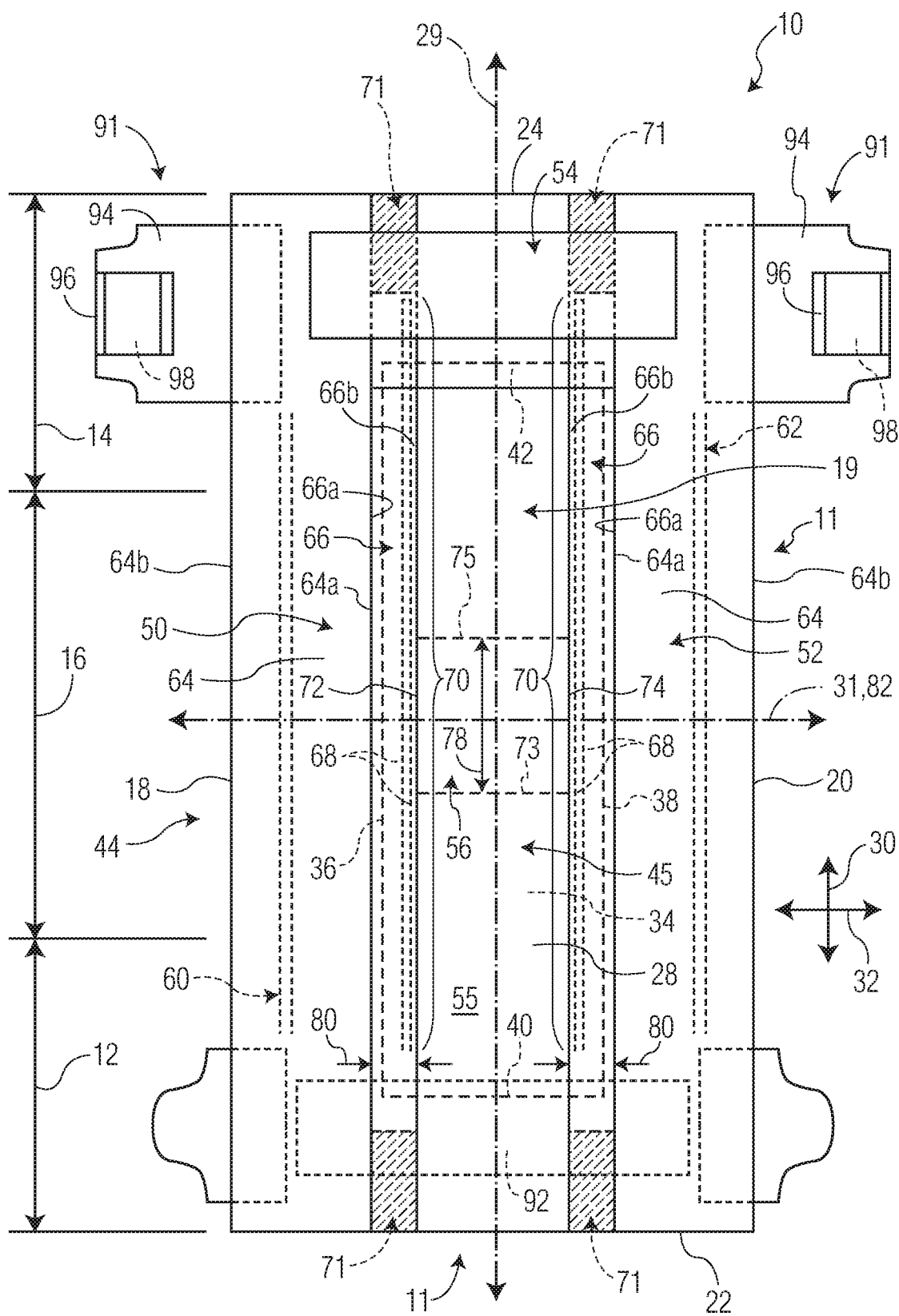
FIG. 2 is a top plan view of the absorbent article of FIG. 1 in a stretched, laid flat, unfastened condition.
Figure 9:
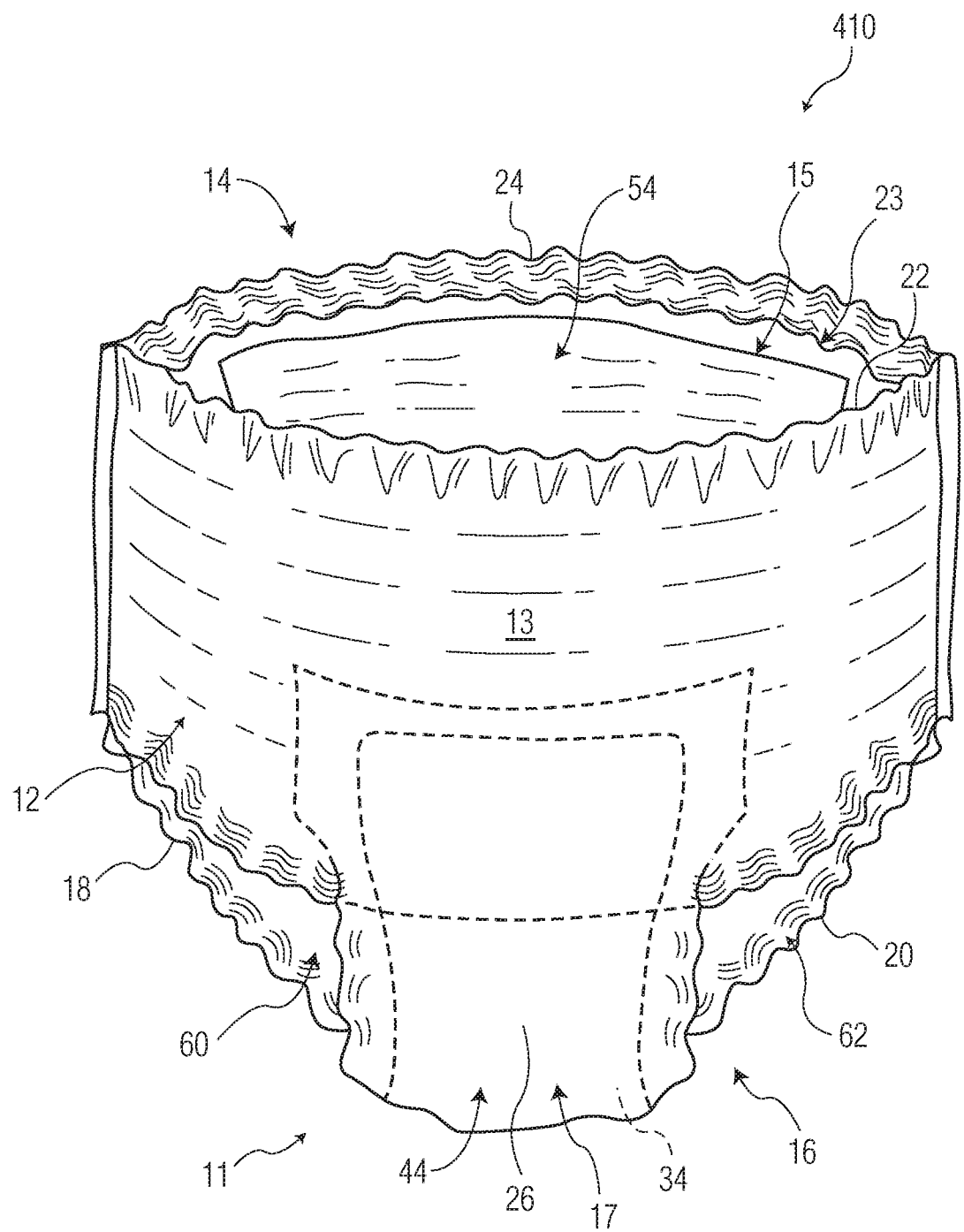
FIG. 9 is a front perspective view of an alternative embodiment of an absorbent article, such as a pant.
Figure 10:
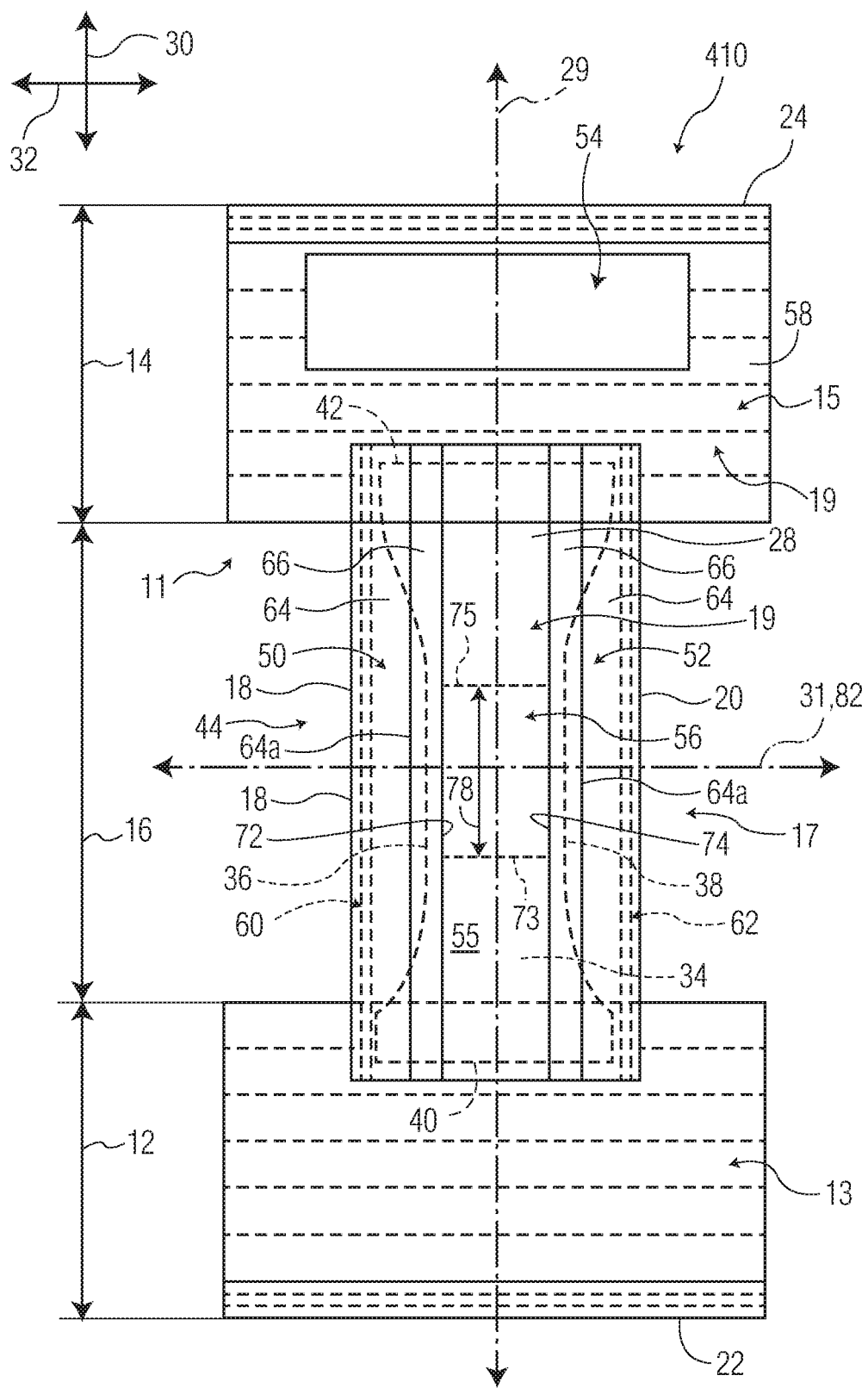
FIG. 10 is a top plan view of the absorbent article of FIG. 9 in a stretched, laid flat condition.

The absorbent article 10 illustrated in FIGS. 1 and 2 and the absorbent article 410 in FIGS. 9 and 10 can each include a chassis 11. The absorbent article 10, 410 can include a front waist region 12, a rear waist region 14, and a crotch region 16 disposed between the front waist region 12 and the rear waist region 14 and interconnecting the front and rear waist regions, 12, 14, respectively. The front waist region 12 can be referred to as the front end region, the rear waist region 14 can be referred to as the rear end region, and the crotch region 16 can be referred to as the intermediate region. In the embodiment depicted in FIGS. 9 and 10, a three-piece construction of an absorbent article 410 is depicted where the absorbent article 410 can have a chassis 11 including a front waist panel 13 defining the front waist region 12, a rear waist panel 15 defining the rear waist region 14, and an absorbent panel 17 defining the crotch region 16 of the absorbent article 110. The absorbent panel 17 can extend between the front waist panel 13 and the rear waist panel 15. In some embodiments, the absorbent panel 17 can overlap the front waist panel 13 and the rear waist panel 15. The absorbent panel 17 can be bonded to the front waist panel 13 and the rear waist panel 15 to define a three-piece construction. However, it is contemplated that an absorbent article can be manufactured in a cross-direction without being a three-piece construction garment.

The absorbent article 10, 410 can have a pair of longitudinal side edges 18, 20, and a pair of opposite waist edges, respectively designated front waist edge 22 and rear waist edge 24. The front waist region 12 can be contiguous with the front waist edge 22 and the rear waist region 14 can be contiguous with the rear waist edge 24. The longitudinal side edges 18, 20 can extend from the front waist edge 22 to the rear waist edge 24. The longitudinal side edges 18, 20 can extend in a direction parallel to the longitudinal direction 30 for their entire length, such as for the absorbent articles 10, 410 illustrated in FIGS. 2 and 10. In other embodiments, the longitudinal side edges 18, 20 can be curved between the front waist edge 22 and the rear waist edge 24. In the absorbent article 410 of FIGS. 9 and 10, the longitudinal side edges 18, 20 can include portions of the front waist panel 13, the absorbent panel 17, and the rear waist panel 15.

The front waist region 12 can include the portion of the absorbent article 10, 410 that, when worn, is positioned at least in part on the front of the wearer while the rear waist region 14 can include the portion of the absorbent article 10, 410 that, when worn, is positioned at least in part on the back of the wearer. The crotch region 16 of the absorbent article 10, 410 can include the portion of the absorbent article 10, 410 that, when worn, is positioned between the legs of the wearer and can partially cover the lower torso of the wearer. The waist edges, 22 and 24, of the absorbent article 10, 410 are configured to encircle the waist of the wearer and together define a central waist opening 23 (as labeled in FIG. 1 and FIG. 9) for the waist of the wearer. Portions of the longitudinal side edges 18, 20 in the crotch region 16 can generally define leg openings for the legs of the wearer when the absorbent article 10, 410 is worn.

The absorbent article 10, 410 can include an outer cover 26 and a bodyside liner 28. The outer cover 26 and the bodyside liner 28 can form a portion of the chassis 11. In an embodiment, the bodyside liner 28 can be bonded to the outer cover 26 in a superposed relation by any suitable means such as, but not limited to, adhesives, ultrasonic bonds, thermal bonds, pressure bonds, or other conventional techniques. The outer cover 26 can define a length in a longitudinal direction 30, and a width in the lateral direction 32, which, in the illustrated embodiment, can coincide with the length and width of the absorbent article 10, 410. As illustrated in FIGS. 2 and 10, the absorbent article 10, 410 can have a longitudinal axis 29 extending in the longitudinal direction 30 and a lateral axis 31 extending in the lateral direction 32.

The chassis 11 can include an absorbent body 34. The absorbent body 34 can be disposed between the outer cover 26 and the bodyside liner 28. The absorbent body 34 can have longitudinal edges, 36 and 38, which, in an embodiment, can form portions of the longitudinal side edges, 18 and 20, respectively, of the absorbent article 10, 410. The absorbent body 34 can have a first end edge 40 that is opposite a second end edge 42, respectively, which, in an embodiment, can form portions of the waist edges, 22 and 24, respectively, of the absorbent article 10, 410. In some embodiments, the first end edge 40 can be in the front waist region 12. In some embodiments, the second end edge 42 can be in the rear waist region 14. In an embodiment, the absorbent body 34 can have a length and width that are the same as or less than the length and width of the absorbent article 10, 410. The bodyside liner 28, the outer cover 26, and the absorbent body 34 can form part of an absorbent assembly 44. In the absorbent article 410 of FIGS. 9 and 10, the absorbent panel 17 can form the absorbent assembly 44. The absorbent assembly 44 can also include a fluid transfer layer 46 (shown in FIGS. 4A-4C) and a fluid acquisition layer 48 (shown in FIGS. 4A-4C) between the bodyside liner 28 and the absorbent body 34. In some embodiments, if a fluid transfer layer 46 is present, the acquisition layer 48 can be between the bodyside liner 28 and the fluid transfer layer 46 as is known in the art. The absorbent assembly 44 can also include a spacer layer (not shown) disposed between the absorbent body 34 and the outer cover 26 as is known in the art. The absorbent assembly 44 can include other components in some embodiments. It is also contemplated that some embodiments may not include a fluid transfer layer 46, and/or an acquisition layer 48, and/or a spacer layer.

The absorbent article 10, 410 can be configured to contain and/or absorb liquid, solid, and semi-solid body exudates discharged from the wearer. In some embodiments, a pair of containment flaps 50, 52 can be configured to provide a barrier to the lateral flow of body exudates. To further enhance containment and/or absorption of body exudates, the absorbent article 10, 410 can suitably include one or more barrier regions 56 formed by the bodyside liner 28. As will be described in further detail below, the barrier region 56 can be formed by the body facing surface 55 of the bodyside liner 28. In some embodiments, the absorbent article 10, 410 can include a waist containment member 54. The waist containment member 54 can be disposed in the rear waist region 14 of the absorbent article 10, 410. Although not depicted herein, it is contemplated that the waist containment member 54 can be additionally or alternatively disposed in the front waist region 12 of the absorbent article 10, 410.

The absorbent article 10, 410 can further include leg elastic members 60, 62 as are known to those skilled in the art. The leg elastic members 60, 62 can be attached to the outer cover 26 and/or the bodyside liner 28 along the opposite longitudinal side edges, 18 and 20, and positioned in the crotch region 16 of the absorbent article 10, 410. The leg elastic members 60, 62 can be parallel to the longitudinal axis 29 as shown in FIGS. 2 and 10 or can be curved as is known in the art. The leg elastic members 60, 62 can provide elasticized leg cuffs.

Additional details regarding each of these elements of the absorbent article 10, 410 described herein can be found below and with reference to the FIGS. 1 through 10.

Outer Cover:

The outer cover 26 and/or portions thereof can be breathable and/or liquid impermeable. The outer cover 26 and/or portions thereof can be elastic, stretchable, or non-stretchable. The outer cover 26 may be constructed of a single layer, multiple layers, laminates, spunbond fabrics, films, meltblown fabrics, elastic netting, microporous webs, bonded-carded webs or foams provided by elastomeric or polymeric materials. In an embodiment, for example, the outer cover 26 can be constructed of a microporous polymeric film, such as polyethylene or polypropylene.

In an embodiment, the outer cover 26 can be a single layer of a liquid impermeable material, such as a polymeric film. In an embodiment, the outer cover 26 can be suitably stretchable, and more suitably elastic, in at least the lateral direction 32 of the absorbent article 10, 410. In an embodiment, the outer cover 26 can be stretchable, and more suitably elastic, in both the lateral 32 and the longitudinal 30 directions. In an embodiment, the outer cover 26 can be a multi-layered laminate in which at least one of the layers is liquid impermeable. In some embodiments, the outer cover 26 can be a two layer construction, including an outer layer (not shown) and an inner layer (not shown) which can be bonded together such as by a laminate adhesive. Suitable laminate adhesives can be applied continuously or intermittently as beads, a spray, parallel swirls, or the like, but it is to be understood that the inner layer can be bonded to the outer layer by other bonding methods, including, but not limited to, ultrasonic bonds, thermal bonds, pressure bonds, or the like.

The outer layer of the outer cover 26 can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer of an outer cover 26 can be a 20 gsm spunbond polypropylene non-woven web. The outer layer may also be constructed of the same materials from which the bodyside liner 28 can be constructed as described herein.

The liquid impermeable inner layer of the outer cover 26 (or the liquid impermeable outer cover 26 where the outer cover 26 is of a single-layer construction) can be either vapor permeable (i.e., "breathable") or vapor impermeable. The liquid impermeable inner layer (or the liquid impermeable outer cover 26 where the outer cover 26 is of a single-layer construction) can be manufactured from a thin plastic film. The liquid impermeable inner layer (or the liquid impermeable outer cover 26 where the outer cover 26 is of a single-layer construction) can inhibit liquid body exudates from leaking out of the absorbent article 10, 410 and wetting articles, such as bed sheets and clothing, as well as the wearer and caregiver.

In some embodiments, where the outer cover 26 is of a single layer construction, it can be embossed and/or matte finished to provide a more cloth-like texture or appearance. The outer cover 26 can permit vapors to escape from the absorbent article 10, 410 while preventing liquids from passing through. A suitable liquid impermeable, vapor permeable material can be composed of a microporous polymer film or a non-woven material which has been coated or otherwise treated to impart a desired level of liquid impermeability.

Absorbent Body:

The absorbent body 34 can be suitably constructed to be generally compressible, conformable, pliable, non-irritating to the wearer's skin and capable of absorbing and retaining liquid body exudates. The absorbent body 34 can be manufactured in a wide variety of sizes and shapes (for example, rectangular, trapezoidal, T-shape, I-shape, hourglass shape, etc.) and from a wide variety of materials. The size and the absorbent capacity of the absorbent body 34 should be compatible with the size of the intended wearer (infants to adults) and the liquid loading imparted by the intended use of the absorbent article 10, 410. The absorbent body 34 can have a length and width that can be less than or equal to the length and width of the absorbent article 10, 410.

In an embodiment, the absorbent body 34 can be composed of a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In an embodiment, the absorbent body 34 can be a matrix of cellulosic fluff and superabsorbent material. In an embodiment, the absorbent body 34 may be constructed of a single layer of materials, or in the alternative, may be constructed of two or more layers of materials.

Various types of wettable, hydrophilic fibers can be used in the absorbent body 34. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. Suitable superabsorbent materials can be selected from natural, synthetic, and modified natural polymers and materials. The superabsorbent materials can be inorganic materials, such as silica gels, or organic compounds, such as cross-linked polymers. In an embodiment, the absorbent body 34 can be free of superabsorbent material.

If a spacer layer is present, the absorbent body 34 can be disposed on the spacer layer and superposed over the outer cover 26. The spacer layer can be bonded to the outer cover 26, for example, by adhesive. In some embodiments, a spacer layer may not be present and the absorbent body 34 can directly contact the outer cover 26 and can be directly bonded to the outer cover 26. However, it is to be understood that the absorbent body 34 may be in contact with, and not bonded with, the outer cover 26 and remain within the scope of this disclosure. In an embodiment, the outer cover 26 can be composed of a single layer and the absorbent body 34 can be in contact with the singer layer of the outer cover 26. In some embodiments, at least a portion of a layer, such as but not limited to, a fluid transfer layer 46 and/or a spacer layer, can be positioned between the absorbent body 34 and the outer cover 26. The absorbent body 34 can be bonded to the fluid transfer layer 46 and/or the spacer layer.

Bodyside Liner:

The bodyside liner 28 of the absorbent article 10, 410 can overlay the absorbent body 34 and the outer cover 26 and can be configured to receive insults of exudates from the wearer and can isolate the wearer's skin from liquid waste retained by the absorbent body 34. The bodyside liner 28 can from at least a part of the body facing surface 19 of the chassis 11.

Figure 4A:
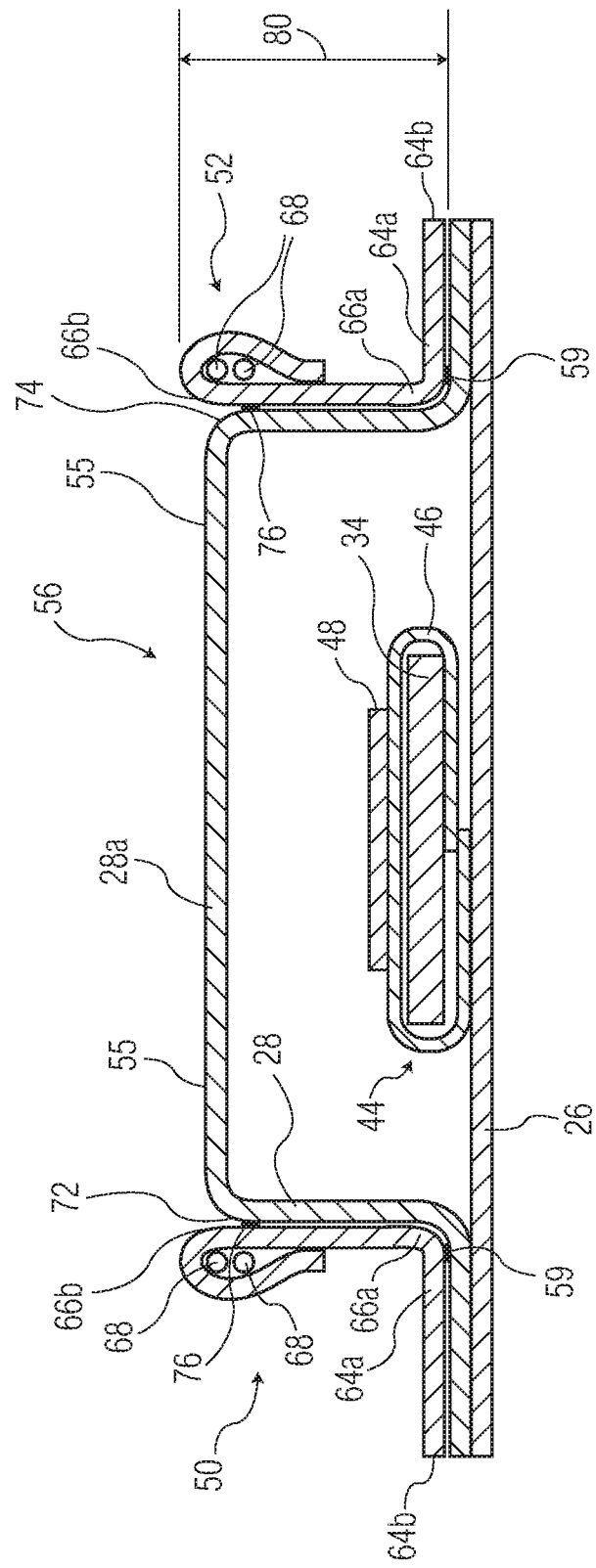
FIG. 4A is a cross-sectional view taken along line 4A-4A from FIG. 3.
Figure 4B:
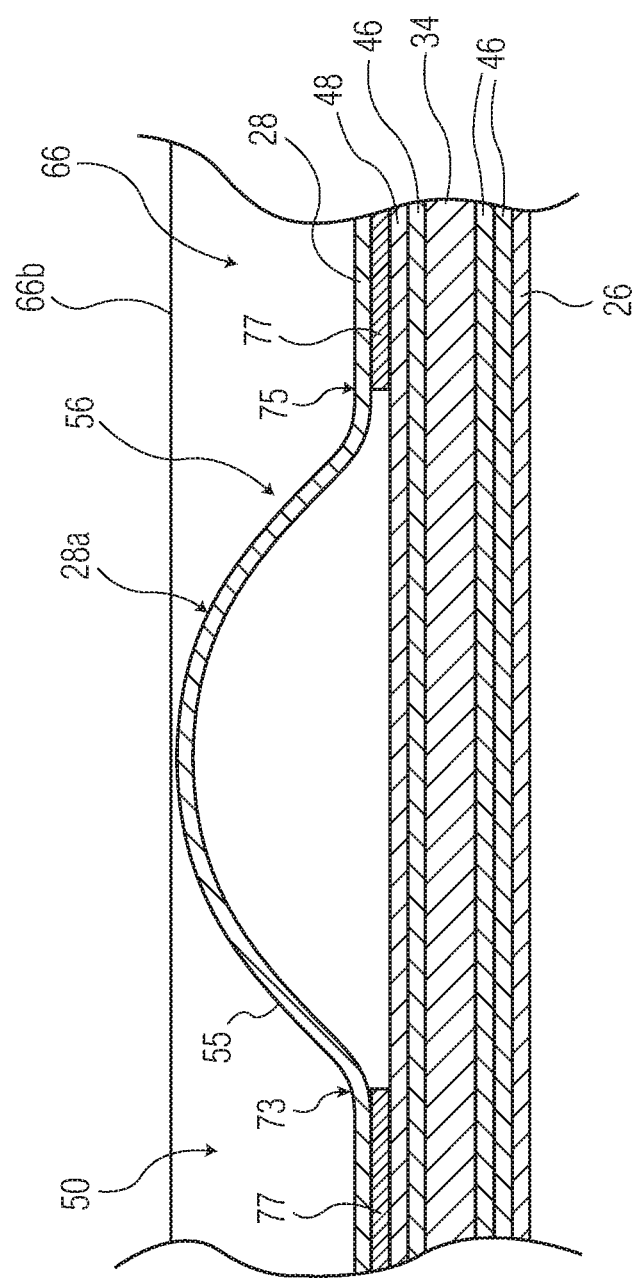
FIG. 4B is a cross-sectional view taken along line 4B-4B from FIG. 3.
Figure 4C:
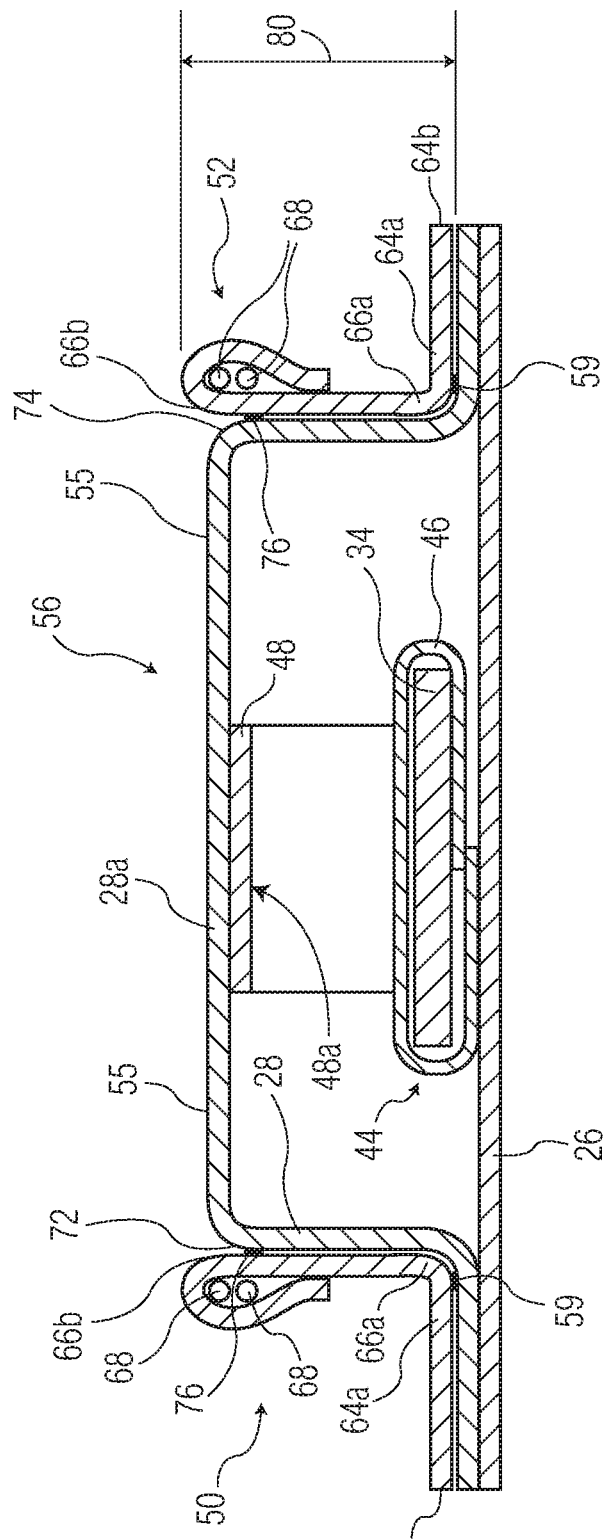
FIG. 4C is a cross-sectional view similar to FIG. 4A, but illustrating an alternative embodiment of the barrier region including the acquisition layer.

In various embodiments, a fluid transfer layer 46 can be positioned between the bodyside liner 28 and the absorbent body 34 (as shown in FIGS. 4A-4C). In various embodiments, an acquisition layer 48 can be positioned between the bodyside liner 28 and the absorbent body 34 or a fluid transfer layer 46, if present (as shown in FIGS. 4A-4C). In various embodiments, the bodyside liner 28 can be bonded to the acquisition layer 48, or to the fluid transfer layer 46 if no acquisition layer 48 is present, via adhesive and/or by a point fusion bonding. The point fusion bonding may be selected from ultrasonic, thermal, pressure bonding, and combinations thereof.

In an embodiment, the bodyside liner 28 can extend beyond the absorbent body 34 and/or a fluid transfer layer 46, if present, and/or an acquisition layer 48, if present, and/or a spacer layer, if present, to overlay a portion of the outer cover 26 and can be bonded thereto by any method deemed suitable, such as, for example, by being bonded thereto by adhesive, to substantially enclose the absorbent body 34 between the outer cover 26 and the bodyside liner 28. In some embodiments, the bodyside liner 28 and the outer cover 26 may be of the same dimensions in width and length. In some embodiments, however, the bodyside liner 28 may be narrower than the outer cover 26 and/or shorter than the outer cover 26. For example, the embodiment of the absorbent article 310 in FIG. 8, described further below, includes a bodyside liner 28 that is shorter than the outer cover 26 in the longitudinal direction 30 of the absorbent article 310 and/or narrower than the outer cover 26 in the lateral direction 32 of the absorbent article 310. In some embodiments, the length of the bodyside liner 28 can range from 50%-100% of the length of the absorbent article 10, 110, 210, 310, 410 as measured in a direction parallel to the longitudinal axis 29, and in some embodiments can range from 50%-95% of the length of the absorbent article 10, 110, 210, 310, 410, can range from 60%-90% of the length of the absorbent article 10, 110, 210, 310, 410. In some embodiments, the bodyside liner 28 can be of greater width than the outer cover 26. It is also contemplated that the bodyside liner 28 may not extend beyond the absorbent body 34 and/or may not be secured to the outer cover 26, such as the embodiment in FIG. 8, where the bodyside liner 28 can be disposed on top of and secured to a secondary liner 27. In some embodiments, the bodyside liner 28 can wrap at least a portion of the absorbent body 34, including wrapping around both longitudinal edges 36, 38 of the absorbent body 34, and/or one or more of the end edges 40, 42. It is further contemplated that the bodyside liner 28 may be composed of more than one segment of material.

The bodyside liner 28 can be of different shapes, including rectangular, hourglass, or any other shape. The bodyside liner 28 can be suitably compliant, soft feeling, and non-irritating to the wearer's skin and can be the same as or less hydrophilic than the absorbent body 34 to permit body exudates to readily penetrate through to the absorbent body 34 and provide a relatively dry surface to the wearer.

The bodyside liner 28 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Figure 8:
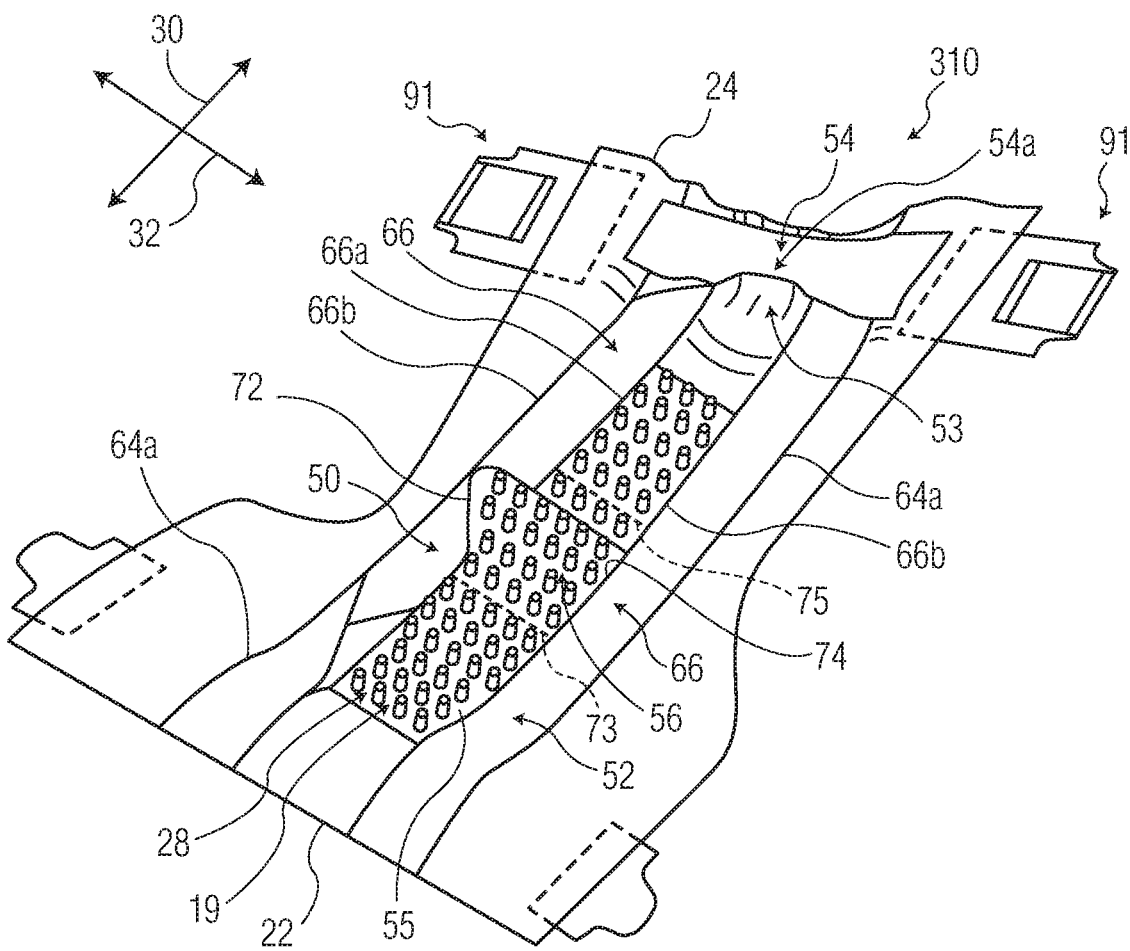
FIG. 8 is a top perspective view of a further alternative embodiment of an absorbent article in an unfastened, relaxed condition.

Various woven and non-woven fabrics can be used for the bodyside liner 28. The bodyside liner 28 can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spunlace, or the like, as well as combinations thereof. The bodyside liner 28 need not be a unitary layer structure, and thus, can include more than one layer of fabrics, films, and/or webs, as well as combinations thereof. For example, the bodyside liner 28 can include a support layer and a projection layer that can be hydroentagled. The projection layer can include hollow projections, such as those disclosed in U.S. Pat. No. 9,474,660 invented by Kirby, Scott S. C. et al., and as depicted in FIG. 8.

For example, the bodyside liner 28 can be composed of a meltblown or spunbond web of polyolefin fibers. Alternatively, the bodyside liner 28 can be a bonded-carded web composed of natural and/or synthetic fibers. The bodyside liner 28 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner 28 or it can be selectively applied to particular sections of the bodyside liner 28.

In an embodiment, a bodyside liner 28 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a bodyside liner 28 can be a spunbond substrate with a basis weight from about 10 or 12 to about 15 or 20 gsm. In an embodiment, a bodyside liner 28 can be a 12 gsm spunbond-meltblown-spunbond substrate having 10% meltblown content applied between the two spunbond layers.

Although the outer cover 26 and bodyside liner 28 can include elastomeric materials, it is contemplated that the outer cover 26 and the bodyside liner 28 can be composed of materials which are generally non-elastomeric. In an embodiment, the bodyside liner 28 can be stretchable, and more suitably elastic. In an embodiment, the bodyside liner 28 can be suitably stretchable and more suitably elastic in at least the lateral or circumferential direction of the absorbent article 10, 410. In other aspects, the bodyside liner 28 can be stretchable, and more suitably elastic, in both the lateral and the longitudinal directions 32, 30, respectively.

As will be discussed in further detail below, the bodyside liner 28 can provide a barrier region 56 that can act as a barrier to the movement of body exudates.

Containment Flaps:

In an embodiment, the absorbent article 10, 410 can include a pair of containment flaps 50, 52. The containment flaps 50, 52 can be formed separately from the absorbent chassis 11 and attached to the chassis 11 or can be formed integral to the chassis 11. In some embodiments, the containment flaps 50, 52 can be secured to the chassis 11 of the absorbent article 10, 410 in a generally parallel, spaced relation with each other laterally inward of the leg openings to provide a barrier against the flow of body exudates. One containment flap 50 can be on a first side of the longitudinal axis 29 and the other containment flap 52 can be on a second side of the longitudinal axis 29. In an embodiment, the containment flaps 50, 52 can extend generally in a longitudinal direction 30 from the front waist region 12 of the absorbent article 10, 410, through the crotch region 16 to the rear waist region 14 of the absorbent article 10, 410. In some embodiments, the containment flaps 50, 52 can extend in a direction substantially parallel to the longitudinal axis 29 of the absorbent article 10, 110, however, in other embodiments, the containment flaps 50, 52 can be curved, as is known in the art. In other embodiments, such as the absorbent article 410 in FIGS. 9 and 10, the containment flaps 50, 52 can be disposed on the absorbent panel 17 in the crotch region 16.

Figure 6:
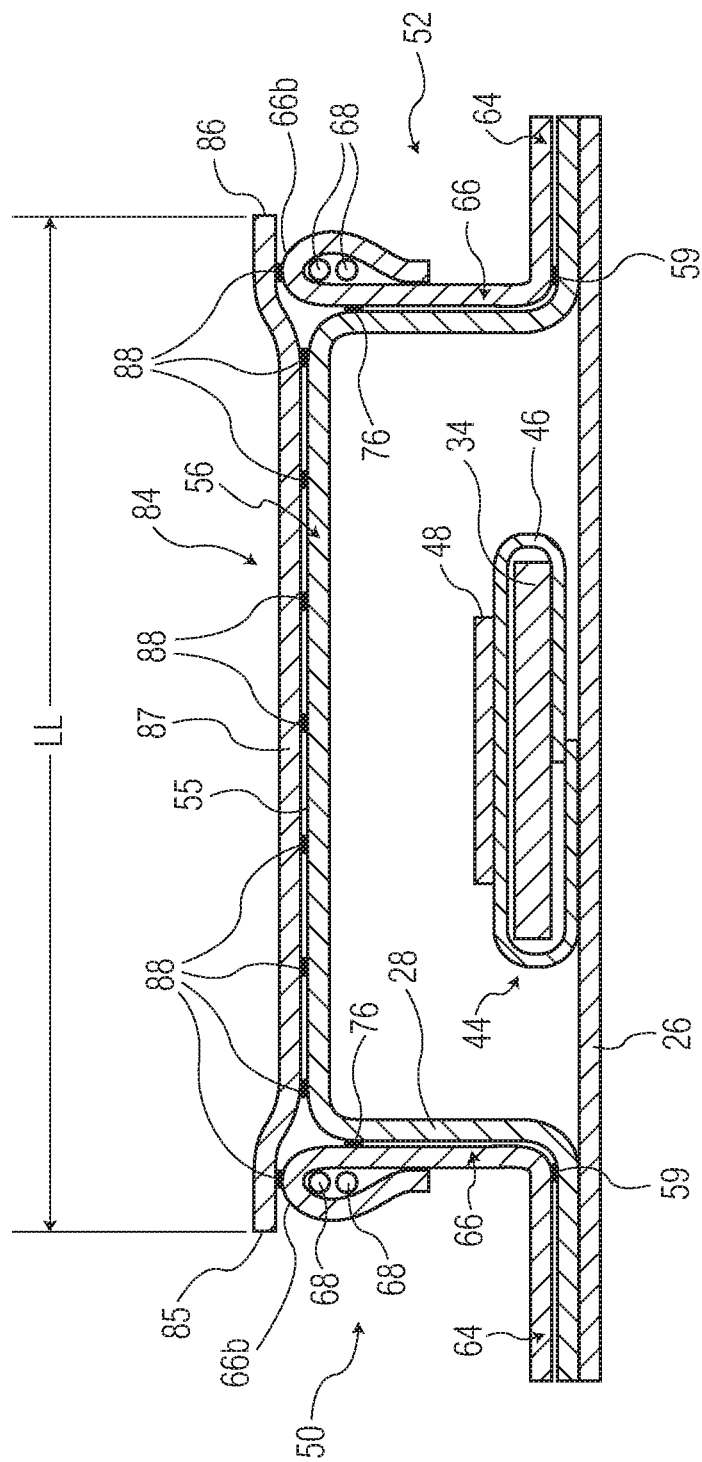
FIG. 6 is a cross-sectional view taken along line 5-5 from FIG. 4.

In embodiments where the containment flaps 50, 52 are coupled to the chassis 11, the containment flaps 50, 52 can be bonded to the bodyside liner 28, the outer cover 26, or another layer, such as a spacer layer, if present, with a barrier adhesive 59, as is known in the art and as depicted in FIGS. 4A, 4C and 6. Of course, the containment flaps 50, 52 can be bonded to other components of the chassis 11 and can be bonded with other suitable means other than a barrier adhesive. For example, the containment flaps 50, 52 can be bonded to the bodyside liner 28, the outer cover 26, or another layer with pressure bonding, thermal bonding, or ultrasonic bonding. The containment flaps 50, 52 can be constructed of a fibrous material which can be similar to the material forming the bodyside liner 28. Other conventional materials, such as polymer films, can also be employed.

As illustrated in FIGS. 2 and 10, the containment flaps 50, 52 can each include a base portion 64 and a projection portion 66. The base portion 64 can be bonded to the chassis 11, for example, to the bodyside liner 28 or the outer cover 26 as mentioned above. The base portion 64 could be bonded to other components of the chassis 11, such as a secondary liner 27 as in the absorbent article 310 of FIG. 8. The base portion 64 can include a proximal end 64a and a distal end 64b. The projection portion 66 can include a proximal end 66a and a distal end 66b. The projection portion 66 can be separated from the base portion 64 at the proximal end 64a of the base portion 64 and the proximal end 66a of the projection portion 66. As used in this context, the projection portion 66 is separated from the base portion 64 in that the proximal end 64a of the base portion 64 and the proximal end 66a of the projection portion 66 defines a transition between the projection portion 66 and the base portion 64. The proximal end 64a of the base portion 64 can be located where the respective containment flap 50, 52 is bonded to the chassis 11 at the most laterally inward location. For example, if a barrier adhesive 59 bonds the base portion 64 to the bodyside liner 28, then the proximal end 64a of the base portion 64 of each containment flap 50, 52 can be located adjacent the barrier adhesive 59. In some embodiments, such as the embodiments illustrated in FIGS. 2 and 10, the distal ends 64b of the base portion 64 can laterally extend to the respective longitudinal side edges 18, 20 of the absorbent article 10, 410. In other embodiments, the distal ends 64b of the base portion 64 can end laterally inward of the respective longitudinal side edges 18, 20 of the absorbent article 10, 410.

The containment flaps 50, 52 can also each include a projection portion 66 that is configured to extend away from the body facing surface 19 of the chassis 11 at least in the crotch region 16 when the absorbent article 10, 410 is in a relaxed configuration, as illustrated in FIGS. 3, 5, 7, and 8. In other words, the projection portion 66 can be configured to extend away from the absorbent body 34. As shown in FIGS. 2 and 10, the containment flaps 50, 52 can include a tack-down region 71 in either or both of the front waist region 12 and the rear waist region 14 where the projection portion 66 is coupled to the body facing surface 19 of the chassis 11. As is known in the art, one technique employs adhesive in the tack-down region 71 to couple the projection portion 66 of the containment flaps 50, 52 to the body facing surface 19 of the chassis 11.

It is contemplated that the containment flaps 50, 52 can be of various configurations and shapes, and can be constructed by various methods. For example, the containment flaps 50, 52 of FIG. 2 depict a vertical containment flap 50, 52 with a tack-down region 71 in both the front and rear waist regions 12, 14 where the projection portion 66 of each containment flap 50, 52 is tacked down to the bodyside liner 28 towards the longitudinal axis 29 of the absorbent article 10. However, it is contemplated that the containment flaps 50, 52 can include a tack-down region 71 where the projection portion 66 of each of the containment flaps 50, 52 is folded back upon itself and coupled to itself and the bodyside liner 28 in a "C-shape" configuration, as is known in the art and described in U.S. Pat. No. 5,895,382 to Robert L. Popp et al. As yet another alternative, it is contemplated that the containment flaps 50, 52 could be constructed in a "T-shape" configuration, such as described in U.S. patent application Ser. No. 13/900,134 by Robert L. Popp et al., which published as U.S. Patent Application Publication 2014/0350504. Such a configuration can also include a tack-down region 71 in either or both of the front and rear waist regions 12, 14, respectively. Of course, other configurations of containment flaps 50, 52 can be used in the absorbent article 10, 410 and still remain within the scope of this disclosure.

The containment flaps 50, 52 can include one or more flap elastic members 68, such as the two flap elastic strands depicted in FIGS. 2, 4A, 4C, and 6 (omitted in FIG. 10 for purposes of clarity). Suitable elastic materials for the flap elastic members 68 can include sheets, strands or ribbons of natural rubber, synthetic rubber, or thermoplastic elastomeric materials. Of course, while two elastic members 68 are shown in each containment flap 50, 52, it is contemplated that the containment flaps 50, 52 can be configured with one or three or more elastic members 68. Alternatively or additionally, the containment flaps 50, 52 can be composed of a material exhibiting elastic properties itself.

The flap elastic members 68, as illustrated in FIG. 2, can have two strands of elastomeric material extending longitudinally in the projection portion 66 of the containment flaps 50, 52, in generally parallel, spaced relation with each other. The flap elastic members 68 can be within the containment flaps 50, 52 while in an elastically contractible condition such that contraction of the strands gathers and shortens the projection portions 66 of the containment flaps 50, 52 in the longitudinal direction 30. As a result, the elastic members 68 can bias the projection portions 66 of the containment flaps 50, 52 to extend away from the body facing surface 45 of the absorbent assembly 44 in a generally upright orientation of the containment flaps 50, 52, especially in the crotch region 16 of the absorbent article 10, 410, when the absorbent article 10, 410 is in a relaxed configuration. Such an upright orientation of the projection portion 66 of containment flap 50 and the projection portion 66 of containment flap 52 is illustrated in FIGS. 3-8, where the absorbent articles 10, 110, 210, 310 are in a relaxed configuration.

During manufacture of the containment flaps 50, 52 at least a portion of the elastic members 68 can be bonded to the containment flaps 50, 52 while the elastic members 68 are elongated. The percent elongation of the elastic members 68 can be, for example, about 110% to about 350%. In one embodiment, the elastic members 68 can be coated with adhesive while elongated to a specified length prior to attaching to the elastic members 68 to the containment flaps 50, 52. In a stretched condition, the length of the elastic members 68 which have adhesive coupled thereto can provide an active flap elastic region 70 in the containment flaps 50, 52, as labeled in FIG. 2 (omitted in FIG. 10 for purposes of clarity), which will gather upon relaxation of the absorbent article 10, 410. The active flap elastic region 70 of containment flaps 50, 52 can be of a longitudinal length that is less than the length of the absorbent article 10, 410. In this exemplary method of bonding the elastic members 68 to the containment flaps 50, 52, the portion of the elastic members 68 not coated with adhesive, will retract after the elastic members 68 and the absorbent article 10, 410 are cut in manufacturing to form an individual absorbent article 10, 410. As noted above, the relaxing of the elastic members 68 in the active flap elastic region 70 when the absorbent article 10, 410 is in a relaxed condition can cause each containment flap 50, 52 to gather and cause the projection portion 66 of each containment flap 50, 52 to extend away from the body facing surface 19 of the chassis 11 (e.g., the body facing surface 45 of the absorbent assembly 44 or the body facing surface 55 of the bodyside liner 28), as depicted in FIGS. 3-8.

Of course, the elastic members 68 can be bonded to the containment flaps 50, 52 in various other ways as known by those of skill in the art to provide an active flap elastic region 70, which is within the scope of this disclosure. Additionally, the active flap elastic regions 70 can be shorter or longer than depicted herein, including extending to the front waist edge 22 and the rear waist edge 24, and still be within the scope of this disclosure.

Leg Elastics:

Leg elastic members 60, 62 can be secured to the outer cover 26, such as by being bonded thereto by laminate adhesive, generally laterally inward of the longitudinal side edges, 18 and 20, of the absorbent article 10, 410. The leg elastic members 60, 62 can form elasticized leg cuffs that further help to contain body exudates. In an embodiment, the leg elastic members 60, 62 may be disposed between inner and outer layers (not shown) of the outer cover 26 or between other layers of the absorbent article 10, for example, between the base portion 64 of each containment flap 50, 52 and the bodyside liner 28, between the base portion 64 of each containment flap 50, 52 and the outer cover 26, or between the bodyside liner 28 and the outer cover 26. The leg elastic members 60, 62 can be one or more elastic components near each longitudinal side edge 18, 20. For example, the leg elastic members 60, 62 as illustrated herein in FIGS. 2 and 10 each include two elastic strands. A wide variety of elastic materials may be used for the leg elastic members 60, 62. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate. Additionally, it is contemplated that the leg elastic members 60, 62 can be formed with the containment flaps 50, 52, and then attached to the chassis 11 in some embodiments. Of course, the leg elastic members 60, 62 can be omitted from the absorbent article 10, 410 without departing from the scope of this disclosure.

Waist Containment Member:

In an embodiment, the absorbent article 10, 410 can have one or more waist containment members 54. FIGS. 1-3, 5, and 8 illustrate a preferred embodiment of a waist containment member 54 on an absorbent article 10, 110, 310, such as a diaper, and FIGS. 9 and 10 illustrate a preferred embodiment of a waist containment member 54 on an absorbent article 410, such as a pant. The waist containment member 54 can be disposed in the rear waist region 14, while in some embodiments, the waist containment member 54 can be disposed in the front waist region 12. The waist containment member 54 can be disposed on the body facing surface 45 of the absorbent assembly 44. In some embodiments, such as in embodiments illustrated in FIGS. 1-3, and 5, the waist containment member 54 can be disposed on the body facing surface 55 of the bodyside liner 28. However, in some embodiments, such as the absorbent article 310 in FIG. 8, the waist containment member 54 can be disposed on other components such as the secondary liner 27. Additionally, in the absorbent article 410 in FIGS. 9 and 10, the waist containment member 54 can be disposed on the rear waist panel 15. The waist containment member 54 can be coupled to the chassis 11 such that a portion 54a of the waist containment member 54 is free to move with respect to the chassis 11 and can form a pocket 53 to help contain body exudates.

The waist containment member 54 can be comprised of a variety of materials. In a preferred embodiment, the waist containment member 54 can be comprised of a spunbond-meltblown-spunbond ("SMS") material. However it is contemplated that the waist containment member 54 can be comprised of other materials including, but not limited to, a spunbond-film-spunbond ("SFS"), a bonded carded web ("BCW"), or any non-woven material. In some embodiments, the waist containment member 54 can be comprised of a laminate of more than one of these exemplary materials, or other materials. In some embodiments, the waist containment member 54 can be comprised of a liquid impermeable material. In some embodiments, the waist containment member 54 can be comprised of a material coated with a hydrophobic coating. In some embodiments, the waist containment member 54 can include an elastic material to provide additional fit and containment properties to the absorbent article 10, 410. In such an embodiment, suitable elastic materials can include, but are not limited to, sheets, strands or ribbons of natural rubber, synthetic rubber, or thermoplastic elastomeric polymers. The elastic materials can be stretched and bonded to a substrate, bonded to a gathered substrate, or bonded to a substrate and then elasticized or shrunk, for example, with the application of heat, such that elastic retractive forces are imparted to the substrate. It is to be understood, however, that the waist containment member 54 may be omitted from the absorbent article without departing from the scope of this disclosure, such as in the absorbent article 210 of the embodiment depicted in FIG. 7.

Barrier Region:

The absorbent article 10, 110, 210, 310, 410 can include a bodyside liner 28 providing a barrier region 56. The barrier region 56 can help form a barrier to prevent exudates from spreading along the body facing surface 19 of the chassis 11 and/or leaking from the absorbent article 10, 110, 210, 310, 410, which in turn, can reduce contact of the skin against certain exudates and help to reduce skin irritation. In the embodiment depicted in FIGS. 1-4B, the absorbent article 10 can include a bodyside liner 28 providing a barrier region 56 in the crotch region 16. When a barrier region 56 is disposed in the crotch region 16 of the absorbent article 10, the barrier region 56 can be referred to as a central barrier region. As best shown in FIGS. 4A and 4B, the barrier region 56 can be formed by a portion 28a of the bodyside liner 28 not being coupled to the absorbent body 34 and the fluid acquisition layer 48 (if present), but being coupled to the first and second containment flaps 50, 52. For example, the portion 28a of the bodyside liner 28 not coupled to the absorbent body 34 or the acquisition layer 48 (if present) can be free from attachment adhesive 77 (as shown in FIG. 4B) that is used to bond other portions of the bodyside liner 28 to underlying components of the absorbent article 10, 110, 210, 310, 410. If the barrier region 56 is in the crotch region 16, the portion 28a of the bodyside liner 28 not coupled to the absorbent body and the fluid acquisition layer 48 (if present) can be referred to as a central portion 28a.

The barrier region 56 can include a first longitudinal side edge 72 and a second longitudinal side edge 74. The barrier region 56 can include a front end 73 and a rear end 75. As depicted in FIG. 4B, the front end 73 and the rear end 75 of the barrier region can be defined by a transition point between where the coupling of the bodyside liner 28 to underlying components starts/stops, (e.g., at an edge of the attachment adhesive 77) to define the portion 28a of the bodyside liner 28 not coupled to the absorbent body 34 and the fluid acquisition layer 48 (if present). The portion 28a of the bodyside liner 28 not coupled to the absorbent body 34 and forming the barrier region 28 can be defined by the first longitudinal side edge 72, the second longitudinal side edge 74, the front end 73, and rear end 75, as illustrated in FIGS. 2-4B. As illustrated in FIG. 4B, the bodyside liner 28 can be coupled to one or more underlying layers outside of the portion 28a, such as by an attachment adhesive 77 between the bodyside liner 28 and the fluid acquisition layer 48.

The first longitudinal side edge 72 of the barrier region 56 can be coupled to the projection portion 66 of the first containment flap 50. The second longitudinal side edge 74 of the barrier region 56 can be coupled to the projection portion 66 of the second containment flap 52. Such a configuration allows the central portion 28a of the bodyside liner 28 providing the barrier region 56 to move independently from the absorbent body 34 and extend away from the absorbent body 34 when the absorbent article 10 is in the relaxed configuration (as illustrated in FIGS. 3, 4A-4C) and the projection portion 66 of the first containment flap 50 and the projection portion 66 of the second containment flap 52 extend away from the absorbent body 34.

Figure 3:
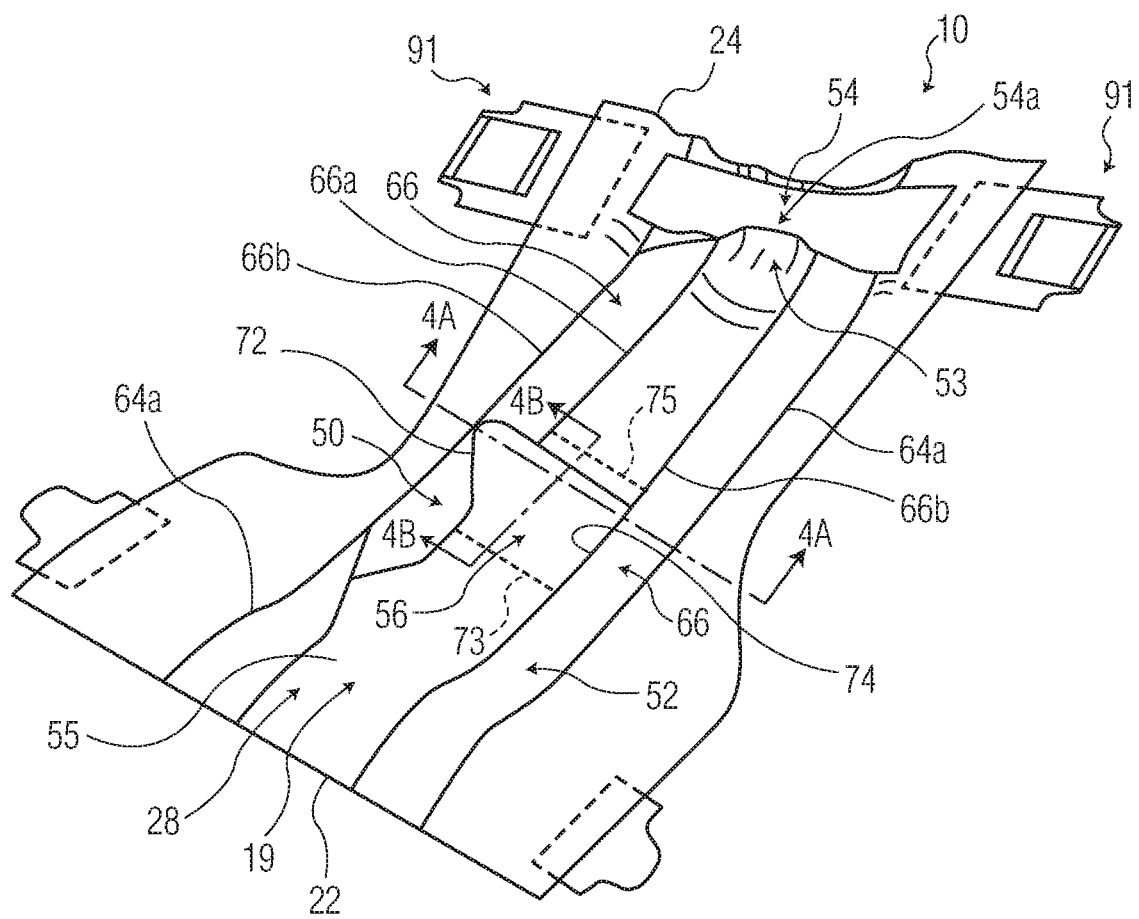
FIG. 3 is a top perspective view of the absorbent article of FIG. 2 in an unfastened, relaxed condition.

As illustrated in FIGS. 3 and 4A, the first longitudinal side edge 72 of the barrier region 56 can be coupled to the projection portion 66 of the first containment flap 50 adjacent a distal end 66b of the projection portion 66 of the first containment flap 50. The second longitudinal side edge 74 of the barrier region 56 can be coupled to the projection portion 66 of the second containment flap 52 adjacent a distal end 66b of the projection portion 66 of the second containment flap 52. As illustrated in FIGS. 4A and 4C, the first longitudinal side edge 72 and the second longitudinal side edge 74 of the barrier region 56 can be coupled to the distal ends 66b of the projection portions 66 of the first and second containment flaps 50, 52, respectively, by an adhesive 76. The adhesive 76 can be applied to the first and second containment flaps 50, 52 and/or to the body facing surface 55 of the bodyside liner 28. Of course, it is contemplated that the first longitudinal side edge 72 and the second longitudinal side edge 74 of the barrier region 56 can be coupled to the distal ends 66b of the projection portions 66 of the first and second containment flaps 50, 52, respectively, by other methods of coupling, including, but not limited to, pressure bonding, ultrasonic bonding, thermal bonding, and/or stitching.

In some embodiments, such as shown in the alternative embodiment of FIG. 4C, the barrier region 56 can be formed by the bodyside liner 28 and another underlying component. For example, FIG. 4C depicts a similar cross-section view as FIG. 4A, however, the embodiment in FIG. 4C illustrates that the central portion 28a of the bodyside liner 28 forming the barrier region 28 can be coupled to the acquisition layer 48, but not coupled to the absorbent body 34. The acquisition layer 48 can include a central region 48a that is coupled to the bodyside liner 28, such as by adhesive (not shown), but that is not coupled to the absorbent body 34. Thus, the central portion 28a of the bodyside liner 28 and the central region 48a of the acquisition layer 48 can form the barrier region 56. By having a region 48a of the acquisition layer 48 help form the barrier region 56 along with the portion 28a of the bodyside liner 28, the barrier region 56 can be more rigid, which can further help to prevent exudates from moving along the body facing surface 19 of the chassis 11.

Referring back to FIGS. 2 and 10, the barrier region 56 can include a longitudinal length 78 as measured in a direction parallel to the longitudinal axis 29 of the absorbent article 10, 410. In some embodiments, the longitudinal length 78 of the barrier region 56 can range from about 5.0 mm to about 300 mm, preferably from about 5.0 mm to about 200.0 mm, and more preferably from about 50.0 mm to about 150.0 mm. The projection portion 66 of the containment flaps 50, 52 can each include a lateral length 80. In preferred embodiments, the lateral length 80 of the projection portion 66 of the first containment flap 50 can be substantially equal to the lateral length of the projection portion 66 of the second containment flap 52. In some embodiments, the lateral length 80 of the projection portion 66 of each containment flap 50, 52 can range from about 5.0 mm to about 100.0 mm, preferably from about 10.0 mm to about 75.0 mm, and more preferably from about 25.0 mm to about 50.0 mm. For purposes herein, the longitudinal length 78 of the barrier region 56 and the lateral length 80 of the projection portion 66 of the containment flaps 50, 52 are to be measured when the absorbent article 10, 410 is in the stretched, laid flat configuration such as illustrated in FIGS. 2 and 10. The lateral length 80 of the second containment flap 52 is also labeled in FIG. 4A, which can be equivalent to a standing height of the containment flap 52.

In some preferred embodiments, the longitudinal length 78 of the barrier region 56 can be greater than or equal to at least twice the lateral length 80 of at least one of the projection portions 66 of the first and second containment flaps 50, 52. For example, if the lateral length of the projection portion 66 of the first containment flap 50 is 10.0 mm, the longitudinal length 78 of the barrier region 56 is preferable to be at least 20.0 mm. By having a lateral length 78 of the barrier region 56 that is greater than or equal to at least twice the lateral length 80 of at least one of the projection portions 66 of the first and second containment flaps 50, 52, the barrier region 56 can be allowed to more easily project away from the chassis 11 of the absorbent article 10, 410 and not hinder the projection portion 66 of each containment flap 50, 52 from projecting away from the chassis 11 of the absorbent article 10, 410 when the absorbent article 10, 410 is in the relaxed configuration and applied to a user. In some embodiments, the longitudinal length 78 of the barrier region 56 can be greater than or equal to at least three times the lateral length 80 of at least one of the projection portions 66 of the first and second containment flaps 50, 52. In some embodiments, the longitudinal length 78 of the barrier region 56 can be less than or equal to ten times the lateral length 80 of at least one of the projection portions 66 of the first and second containment flaps 50, 52.

As noted above, the barrier region 56 can be located in the crotch region 16 of the absorbent article 10, 410. In some embodiments, such as the embodiments illustrated in FIGS. 2 and 10, the barrier region 56 can be located about equidistant from the front waist edge 22 and the rear waist edge 24 of absorbent article 10, 410. For purposes herein, the location of the barrier region 56 with respect to the front and rear waist edges 22, 24 can be measured from a lateral axis 82 of the barrier region 56 located centrally between the front end 73 and the rear end 75 of the barrier region 56 and is measured when the absorbent article 10, 410 is in the stretched, laid-flat configuration. In some embodiments, the lateral axis 82 of the barrier region 56 can be co-linear with the lateral axis 31 of the absorbent article 10, 410. However, in some embodiments, it may be preferable to dispose the barrier region 56 such that the lateral axis 82 of the barrier region 56 is located in front of the lateral axis 31 of the absorbent article 10, 410, or in other words, between the lateral axis 31 of the absorbent article 10, 410, and the front waist edge 22 of the absorbent article 10, 410. In other embodiments, it may be preferable to dispose the barrier region 56 such that the lateral axis 82 of the barrier region 56 is located behind the lateral axis 31 of the absorbent article 10, 410, or in other words, between the lateral axis 31 of the absorbent article 10, 410, and the rear waist edge 24 of the absorbent article 10, 410. In some embodiments, it may be preferable to locate the barrier region 56 such that the lateral axis 82 of the barrier region 56 is located a distance from the front waist edge 22 of the absorbent article 10, 410 of between ⅓ to ⅔ of the length of the absorbent article 10, 410 (as measured between the front waist edge 22 and rear waist edge 24 when the absorbent article 10, 410 is in the stretched, laid flat configuration). Such a configuration may allow for the barrier region 56 to be placed approximately half-way in between where the absorbent article 10, 410 is expected to be insulted with a bowel movement and is expected to be insulted with urine from a wearer, regardless of the sex of the wearer.

Figure 5:
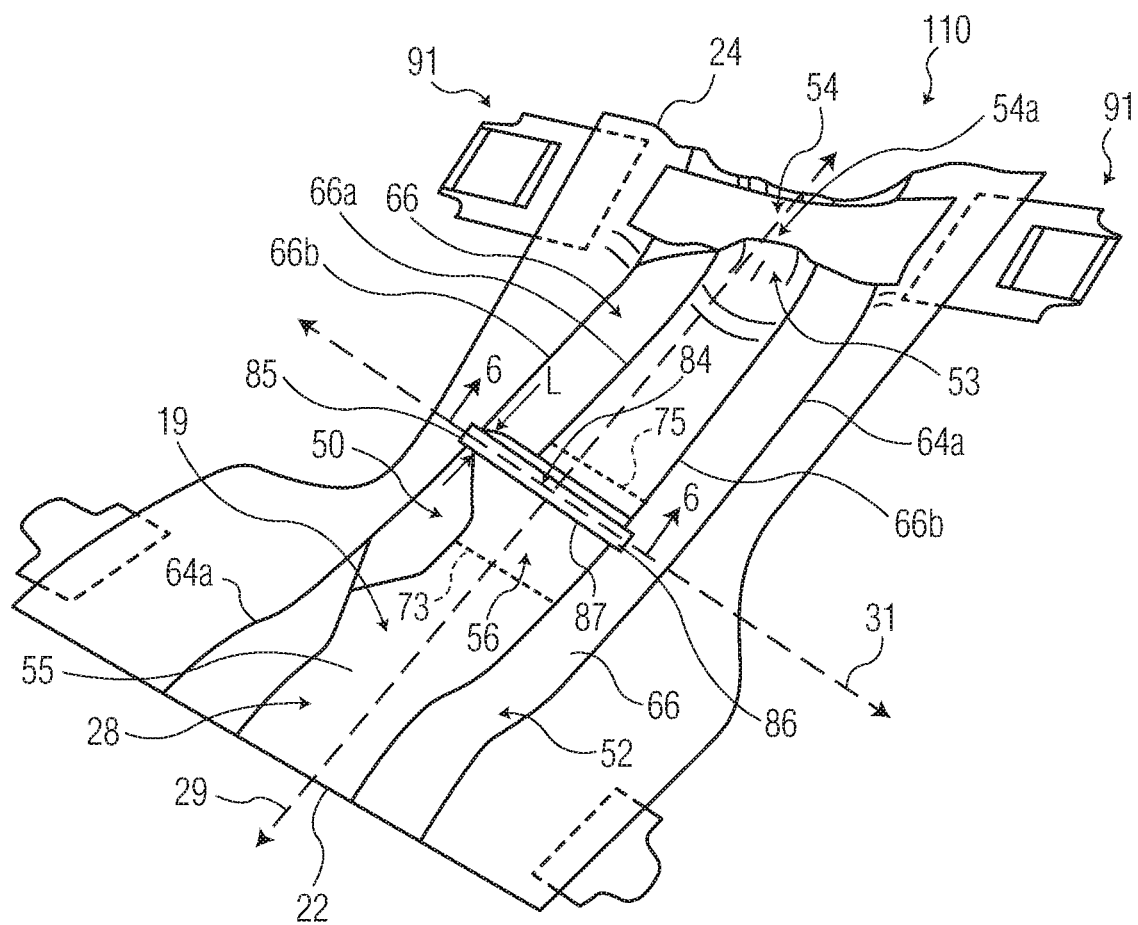
FIG. 5 is a top perspective view of an alternative embodiment of an absorbent article in an unfastened, relaxed condition.

Now turning to FIGS. 5 and 6, another embodiment of an absorbent article 110 including a barrier region 56 is illustrated. In the embodiment illustrated in FIGS. 5 and 6, the absorbent article 110 can include a bodyside liner 28 providing a barrier region 56 similar to that as described above and as illustrated in the embodiment of FIGS. 1-4B or FIG. 4C. The absorbent article 110 of FIGS. 5 and 6, however, can also include a flap connector 84. The flap connector 84 can provide an alternative mechanism or an additional mechanism to aid the barrier region 56 of the bodyside liner 28 in extending away from the absorbent body 34 to help create a barrier to body exudates.

The flap connector 84 can include a first end region 85 and a second end region 86 opposite from the first end region 85. The flap connector 84 can also include a middle portion 87 disposed between the first end region 85 of the flap connector 84 and the second end region 86 of the flap connector 84. The first end region 85 of the flap connector 84 can be coupled to the projection portion 66 of the first containment flap 50. The second end region 86 of the flap connector 84 can be coupled to the projection portion 66 of the second containment flap 50. The middle portion 87 of the flap connector 84 can be coupled to the barrier region 56 provided by the bodyside liner 28. In some embodiments, the first end region 85 of the flap connector 84 can be coupled to the projection portion 66 of the first containment flap 50 and the second end region 86 of the flap connector 84 can be coupled to the projection portion 66 of the second containment flap 50 with an adhesive 88. In some embodiments, the middle portion 87 of the flap connector 84 can be coupled to the barrier region 56 with an adhesive 88. As depicted in FIG. 6, the adhesive 88 in some embodiments can be intermittent, while in other embodiments, the adhesive 88 could be a continuous bead of adhesive. Of course, it is also contemplated that the first end region 85 of the flap connector 84 can be coupled to the projection portion 66 of the first containment flap 50, the second end region 86 of the flap connector 84 can be coupled to the projection portion 66 of the second containment flap 50, and/or the middle portion 87 of the flap connector 84 can be coupled to the barrier region 56 by other methods of coupling, including, but not limited to, pressure bonding, ultrasonic bonding, thermal bonding, and/or stitching. By coupling the flap connector 84 to the containment flaps 50, 52 and the portion 28a of the bodyside liner 28 forming the barrier region 28a, the flap connector 84 can aid the barrier region 56 to move independently from the absorbent body 34 and extend away from the absorbent body 34 when the absorbent article 110 is in the relaxed configuration (as illustrated in FIG. 5) and the projection portion 66 of the first containment flap 50 and the projection portion 66 of the second containment flap 52 extend away from the absorbent body 34.

In some embodiments including a flap connector 84, the first longitudinal side edge 72 of the barrier region 56 can be coupled to the first containment flap 50 (e.g., with adhesive 76) and the second longitudinal side edge 74 of the barrier region 56 can be coupled to the second containment flap 52 (e.g., with adhesive 76) as depicted in FIG. 6. However, in some embodiments including a flap connector 84, it is also contemplated that the barrier region 56 need not be coupled directly to the first containment flap 50 and the second containment flap 52 and still provide a barrier region 56 that extends away from absorbent body 34 when the absorbent article 110 is in the relaxed configuration and the projection portion 66 of the first containment flap 50 and the projection portion 66 of the second containment flap 52 extend away from the absorbent body 34 because the flap connector 84 can aid in extending the portion 28a of the bodyside liner 28 away from the absorbent body 34.

As depicted in FIGS. 5 and 6, the flap connector 84 can include a longitudinal length L as measured in a direction parallel to the longitudinal axis 29 of the absorbent article 110 and a lateral length LL as measured in a direction parallel to the lateral axis 31 of the absorbent article 110. For purposes herein, the longitudinal length L and the lateral length LL of the flap connector 84 is to be measured when the absorbent article 110 is in the stretched, laid flat configuration such as illustrated in the embodiments of the absorbent articles 10, 410 in FIGS. 2 and 10. The longitudinal length L of the flap connector 84 can be less than the longitudinal length 78 of the barrier region 56 as described above. In some embodiments, the longitudinal length L of the flap connector 84 can range from about 1.0 mm to about 50.0 mm, preferably from about 2.0 mm to about 25.0 mm, and more preferably from about 2.0 mm to about 10.0 mm. It is preferable to minimize the longitudinal length L of the flap connector 84, as having a greater longitudinal length L of the flap connector 84 can interfere with insults of exudates from reaching the bodyside liner 28 where intended from exudate origination locations on the wearer. As depicted in FIG. 6, the lateral length LL of the flap connector 84 can be configured such that it can span across the first containment flap 50 to the second containment flap 52 when the absorbent article 110 is in the relaxed configuration and the first containment flap 50 and the second containment flap 52 extend away from the chassis 11.

The flap connector 84 can be comprised of any of a variety of materials. For example, in some embodiments, the flap connector 84 can be made of a spunbond-meltblown-spunbond ("SMS") material. However it is contemplated that the flap connector 84 can be comprised of other materials including, but not limited to, a spunbond-film-spunbond ("SFS"), a bonded carded web ("BCW"), or any non-woven material. In some embodiments, the flap connector 84 can be comprised of a laminate of more than one of these exemplary materials, or other materials. In some embodiments, the flap connector 84 can be comprised of a liquid impermeable and/or a material coated with a hydrophobic coating.

Figure 7:
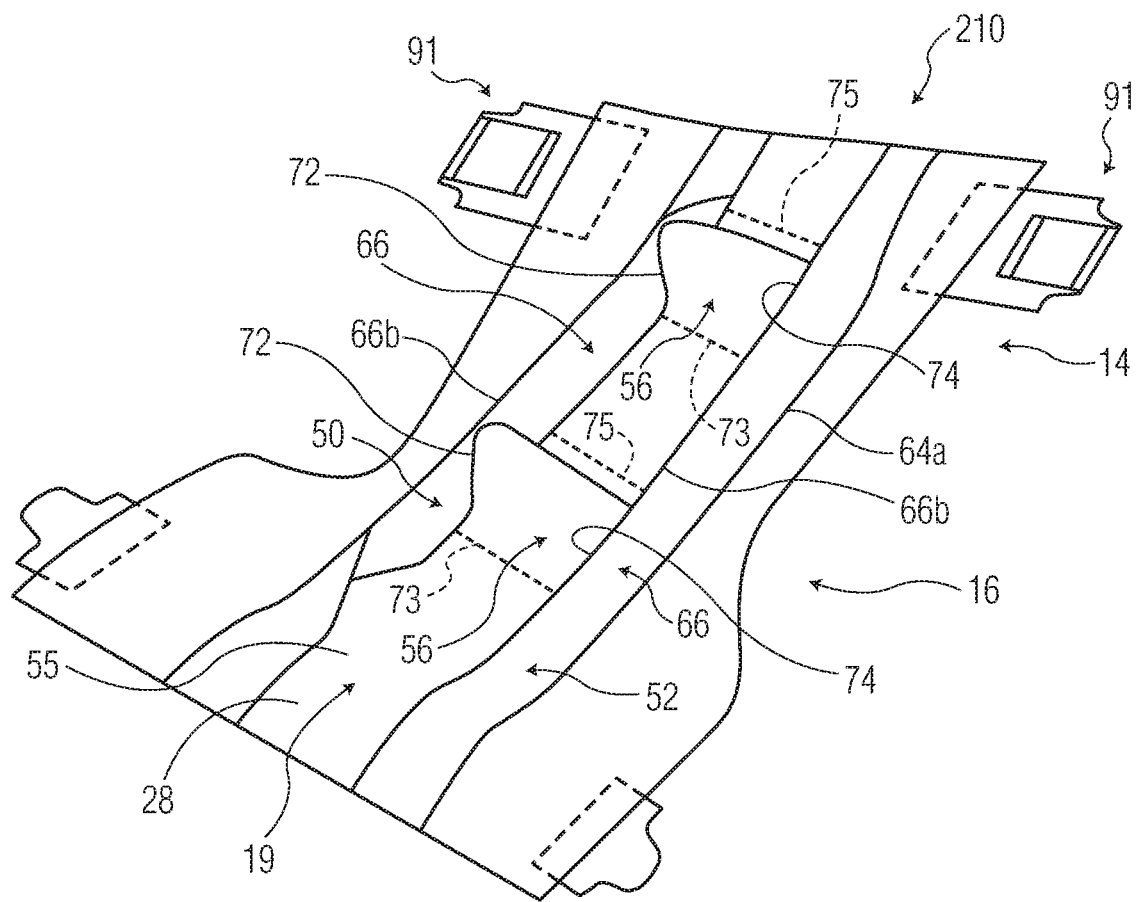
FIG. 7 is a top perspective view of another alternative embodiment of an absorbent article in an unfastened, relaxed condition that includes two barrier regions.

FIG. 7 illustrates another embodiment of an absorbent article 210 that includes more than one barrier region 56. As depicted in FIG. 7, the bodyside liner 28 of the absorbent article 210 provides two barrier regions 56. The bodyside liner 28 of the absorbent article 210 includes a barrier region 56 in the crotch portion 16 (e.g., referred to as a central barrier region) and a barrier region 56 in the rear waist region 14 (e.g., referred to as a rear barrier region). The barrier region 56 disposed in the crotch portion 16 and the barrier region 56 in the rear waist region 14 of the absorbent article 210 can be configured in a similar fashion as discussed above with respect to the barrier region 56 of the absorbent article 10 depicted in FIGS. 1-4B, or the embodiment of the barrier region 56 depicted in FIG. 4C. The barrier region 56 in the rear waist region 14 can provide an additional barrier to the flow of exudates on the absorbent article 210. In such an embodiment, the two barrier regions 56 can form two longitudinal barriers for the flow of body exudates. Such a configuration may be especially advantageous when the absorbent article 210 does not include a waist containment member 54, such as the absorbent article 210 depicted in FIG. 7. Although neither of the two barrier regions 56 of the absorbent article 210 shown in FIG. 7 include a flap connector 84, it is also contemplated that one or both of the barrier regions 56 could include a flap connector 84 in an alternative embodiment. For example, one or both barrier regions 56 could be configured as the embodiment discussed above and depicted in FIGS. 5 and 6, which included a flap connector 84.

If an absorbent article includes more than one barrier region 56, the barrier regions 56 the barrier regions 56 can be configured to be the same, or can vary from one another in one or more aspects. For example, in some embodiments, the barrier regions 56 can be configured to have different longitudinal lengths 78. As another example, the barrier regions 56 can be configured to comprise different materials or coatings.

FIG. 8 depicts yet another embodiment of an absorbent article 310 including a bodyside liner 28 providing a barrier region 56. The barrier region 56 can be configured in the same manner as discussed above with respect to the barrier region 56 of the absorbent article 10 depicted in FIGS. 1-4B, or the embodiment of the barrier region 56 depicted in FIG. 4C. Alternatively, the barrier region 56 could be configured to include a flap connector 84 as discussed above and as depicted in the absorbent article 110 of FIGS. 5 and 6. As depicted in FIG. 8, the bodyside liner 28 providing the barrier region 56 can be shorter than the length of the outer cover 26 in the longitudinal direction 30 and/or a width of the outer cover 26 in the lateral direction 32. The bodyside liner 28 can be shorter than the length absorbent article 310, as measured from the front waist edge 22 to the rear waist edge 24 in a direction parallel to the longitudinal axis 29 when the absorbent article 310 is in the stretched, laid-flat configuration. In some embodiments, the length of the bodyside liner 28 can range from 50%-100% of the length of the absorbent article 10, 110, 210, 310, 410, and in some embodiments can range from 50%-95% of the length of the absorbent article 10, 110, 210, 310, 410, or in some embodiments, can range from 60%-90% of the length of the absorbent article 10, 110, 210, 310, 410. In some embodiments that include a bodyside liner 28 that does not extend the full length of the absorbent article, such as the absorbent article 310 of FIG. 8, the absorbent article 310 can include a secondary liner 27. The secondary liner 27 can extend from the front waist edge 22 to the rear waist edge 24, however, in some embodiments, the secondary liner 27 can be narrower than the length of the absorbent article 310. The secondary liner 27 can be disposed between the absorbent body 34 and the bodyside liner 28. In some embodiments, the containment flaps 50, 52 can be disposed on top of the secondary liner 27.

Fastening System:

In an embodiment, the absorbent article 10, 110, 210, 310 can include a fastening system. The fastening system can include one or more back fasteners 91 and one or more front fasteners 92. The embodiments shown in FIGS. 1-3, 5, 7, and 8 depict embodiments with one front fastener 92. Portions of the fastening system may be included in the front waist region 12, rear waist region 14, or both.

The fastening system can be configured to secure the absorbent article 10, 110, 210, 310 about the waist of the wearer in a fastened condition as shown in FIG. 1 and help maintain the absorbent article 10, 110, 210, 310 in place during use. In an embodiment, the back fasteners 91 can include one or more materials bonded together to form a composite ear as is known in the art. For example, the composite fastener may be composed of a stretch component 94, a nonwoven carrier or hook base 96, and a fastening component 98, as labeled in FIG. 2.

EMBODIMENTS

Embodiment 1

An absorbent article including a front waist region, a rear waist region, a crotch region, a longitudinal axis and a lateral axis, the absorbent article comprising: a chassis including a bodyside liner, an outer cover, and an absorbent body, the absorbent body disposed between the bodyside liner and the outer cover, the bodyside liner including a length that is at least 50% of a length of the absorbent article as measured in a direction parallel to the longitudinal axis; and a pair of containment flaps comprising a first containment flap and a second containment flap, the first containment flap and the second containment flap each extending from the front waist region to the second waist region, the pair of containment flaps each comprising a base portion coupled to the chassis and a projection portion extending away from the absorbent body when the absorbent article is in a relaxed configuration; wherein the bodyside liner comprises a central barrier region in the crotch region, the central barrier region being a central portion of the bodyside liner not coupled to the absorbent body and comprising a first longitudinal side edge and a second longitudinal side edge, the first longitudinal side edge being coupled to the projection portion of the first containment flap and the second longitudinal side edge being coupled to the projection portion of the second containment flap such that when the absorbent article is in the relaxed configuration and the projection portion of the first containment flap and the projection portion of the second containment flap extend away from the absorbent body, the central portion of the bodyside liner extends away from the absorbent body.

Embodiment 2

The absorbent article of embodiment 1, wherein the first longitudinal side edge of the central barrier region is coupled to the projection portion of the first containment flap adjacent a distal end of the projection portion of the first containment flap, and wherein the second longitudinal side edge of the central barrier region is coupled to the projection portion of the second containment flap adjacent a distal end of the projection portion of the second containment flap.

Embodiment 3

The absorbent article of embodiment 1 or 2, wherein the first longitudinal side edge of the central barrier region is coupled to the projection portion of the first containment flap with adhesive, and wherein the second longitudinal side edge of the central barrier region is coupled to the projection portion of the second containment flap with adhesive.

Embodiment 4

The absorbent article of any one of the preceding embodiments, further comprising: a flap connector comprising a first end region, a middle portion, and a second end region, the first end region of the flap connector being coupled to the projection portion of the first containment flap, the second end region of the flap connector being coupled to the projection portion of the second containment flap, and the middle portion of the flap connector being coupled to the central barrier region of the bodyside liner.

Embodiment 5

The absorbent article of embodiment 4, wherein the flap connector comprises a longitudinal length as measured in a direction parallel to the longitudinal axis of the absorbent article and the central barrier region comprises a longitudinal length as measured in the direction parallel to the longitudinal axis of the absorbent article, the longitudinal length of the flap connector being less than the longitudinal length of the central barrier region.

Embodiment 6

The absorbent article of any one of the preceding embodiments, wherein the central barrier region comprises a longitudinal length as measured in a direction parallel to the longitudinal axis of the absorbent article, and the projection portion of the first containment flap and the projection portion of the second containment flap each have a lateral length as measured in a direction parallel to the lateral axis of the absorbent article, and wherein the longitudinal length of the central barrier region is greater than or equal to at least twice the lateral length of the first containment flap or the lateral length of the second containment flap.

Embodiment 7

The absorbent article of any one of the preceding embodiments, wherein the central barrier region comprises a longitudinal length as measured in a direction parallel to the longitudinal axis of the absorbent article, and the longitudinal length of the central barrier region is between about 5.0 mm to about 150.0 mm.

Embodiment 8

The absorbent article of any one of the preceding embodiments, wherein the absorbent article includes a front waist edge in the front waist region and a rear waist edge in the rear waist region, and wherein the central barrier region is located a distance from the front waist edge of between about ⅓ to about ⅔ of the length of the absorbent article.

Embodiment 9

The absorbent article of any one of the preceding embodiments, wherein the bodyside liner further comprises a rear barrier region disposed in the rear waist region of the absorbent article, the rear barrier region being a rear portion of the bodyside liner not coupled to the absorbent body and comprising a first longitudinal side edge and a second longitudinal side edge, the first longitudinal side edge of the rear barrier region being coupled to the projection portion of the first containment flap and the second longitudinal side edge of the rear barrier region being coupled to the projection portion of the second containment flap such that when the absorbent article is in the relaxed configuration and the projection portion of the first containment flap and the projection portion of the second containment flap extend away from the absorbent body, the rear portion of the bodyside liner extends away from the absorbent body.

Embodiment 10

The absorbent article of any one of the preceding embodiments, further comprising an acquisition layer, the acquisition layer being disposed between the absorbent body and the bodyside liner, the central portion of the bodyside liner not being coupled to the acquisition layer.

Embodiment 11

The absorbent article of any one of embodiments 1-9, further comprising an acquisition layer, the acquisition layer being disposed between the absorbent body and the bodyside liner, the central portion of the bodyside liner being coupled to a central region of the acquisition layer, the central region of the acquisition layer not being coupled to the absorbent body.

Embodiment 12

An absorbent article including a front waist region, a rear waist region, a crotch region, a longitudinal axis and a lateral axis, the absorbent article comprising: a chassis including a bodyside liner, an outer cover, and an absorbent body, the absorbent body disposed between the bodyside liner and the outer cover, the bodyside liner including a length that is at least 50% of a length of the absorbent article as measured in a direction parallel to the longitudinal axis; and a pair of containment flaps comprising a first containment flap and a second containment flap, the first containment flap and the second containment flap each extending from the front waist region to the second waist region, the pair of containment flaps each comprising a base portion coupled to the chassis and a projection portion extending away from the absorbent body when the absorbent article is in a relaxed configuration; wherein the bodyside liner comprises a barrier region, the barrier region being a portion of the bodyside liner configured to move independently from the absorbent body and to extend away from the absorbent body when the absorbent article is in the relaxed configuration.

Embodiment 13

The absorbent article of embodiment 12, wherein the barrier region comprises a first longitudinal side edge and a second longitudinal side edge, the first longitudinal side edge being coupled to the projection portion of the first containment flap and the second longitudinal side edge being coupled to the projection portion of the second containment flap.

Embodiment 14

The absorbent article of embodiment 12 or 13 wherein the first longitudinal side edge of the barrier region is coupled to the projection portion of the first containment flap adjacent a distal end of the projection portion of the first containment flap, and wherein the second longitudinal side edge of the central barrier region is coupled to the projection portion of the second containment flap adjacent a distal end of the projection portion of the second containment flap.

Embodiment 15

The absorbent article of any one of embodiments 12-14, wherein the barrier region is disposed in the crotch region of the absorbent article.

Embodiment 16

The absorbent article of any one of embodiments 12-15, further comprising:
a flap connector comprising a first end region, a middle portion, and a second end region, the first end region of the flap connector being coupled to the projection portion of the first containment flap, the second end region of the flap connector being coupled to the projection portion of the second containment flap, and the middle portion of the flap connector being coupled to the barrier region of the bodyside liner.

Embodiment 17

The absorbent article of any one of embodiments 12-16, wherein the barrier region comprises a longitudinal length as measured in a direction parallel to the longitudinal axis of the absorbent article, and the projection portion of the first containment flap and the projection portion of the second containment flap each have a lateral length as measured a direction parallel to the lateral axis of the absorbent article, and wherein the longitudinal length of the barrier region is greater than or equal to at least twice the lateral length of the first containment flap or the lateral length of the second containment flap.

Embodiment 18

The absorbent article of any one of embodiments 12-17, further comprising an acquisition layer, the acquisition layer being disposed between the absorbent body and the bodyside liner, the portion of the bodyside liner forming the barrier region not being coupled to the absorbent body and not being coupled to the acquisition layer.

Embodiment 19

An absorbent article including a front waist region, a rear waist region, a crotch region, a longitudinal axis and a lateral axis, the absorbent article comprising: a chassis including a bodyside liner, an outer cover, and an absorbent body, the absorbent body disposed between the bodyside liner and the outer cover; a pair of containment flaps comprising a first containment flap and a second containment flap, the first containment flap and the second containment flap each extending from the front waist region to the second waist region, the pair of containment flaps each comprising a base portion coupled to the chassis and a projection portion extending away from the absorbent body when the absorbent article is in a relaxed configuration; and a flap connector comprising a first end region, a middle portion, and a second end region; the first end region of the flap connector being coupled to the projection portion of the first containment flap, the second end region of the flap connector being coupled to the projection portion of the second containment flap; wherein the bodyside liner comprises a barrier region in the crotch region of the absorbent article, the barrier region being a portion of the bodyside liner not coupled to the absorbent body and comprising a first longitudinal side edge and a second longitudinal side edge, the barrier region being coupled to the middle portion of the flap connector; and wherein the flap connector and the barrier region are configured such that when the absorbent article is in the relaxed configuration and the projection portion of the first containment flap and the projection portion of the second containment flap extend away from the absorbent body, the flap connector and the portion of the bodyside liner not coupled to the absorbent body extend away from the absorbent body.

Embodiment 20

The absorbent article of embodiment 19, wherein the flap connector comprises a longitudinal length as measured in a direction parallel to the longitudinal axis of the absorbent article, the longitudinal length of the flap connector being between about 1.0 mm to about 10.0 mm.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. An absorbent article including a front waist region, a rear waist region, a crotch region, a longitudinal axis and a lateral axis, the absorbent article comprising:
a chassis including a bodyside liner, an outer cover, and an absorbent body, the absorbent body disposed between the bodyside liner and the outer cover, the bodyside liner including a length that is at least 50% of a length of the absorbent article as measured in a direction parallel to the longitudinal axis; and
a pair of containment flaps comprising a first containment flap and a second containment flap, the first containment flap and the second containment flap each extending from the front waist region to the second waist region, the pair of containment flaps each comprising a base portion coupled to the chassis and a projection portion extending away from the absorbent body when the absorbent article is in a relaxed configuration;
wherein the bodyside liner comprises a central barrier region in the crotch region, the central barrier region being a central portion of the bodyside liner not coupled to the absorbent body and comprising a first longitudinal side edge and a second longitudinal side edge, the first longitudinal side edge being coupled to the projection portion of the first containment flap and the second longitudinal side edge being coupled to the projection portion of the second containment flap such that when the absorbent article is in the relaxed configuration and the projection portion of the first containment flap and the projection portion of the second containment flap extend away from the absorbent body, the central portion of the bodyside liner extends away from the absorbent body.

2. The absorbent article of claim 1, wherein the first longitudinal side edge of the central barrier region is coupled to the projection portion of the first containment flap adjacent a distal end of the projection portion of the first containment flap, and wherein the second longitudinal side edge of the central barrier region is coupled to the projection portion of the second containment flap adjacent a distal end of the projection portion of the second containment flap.

3. The absorbent article of claim 1, wherein the first longitudinal side edge of the central barrier region is coupled to the projection portion of the first containment flap with adhesive, and wherein the second longitudinal side edge of the central barrier region is coupled to the projection portion of the second containment flap with adhesive.

4. The absorbent article of claim 1, further comprising:
a flap connector comprising a first end region, a middle portion, and a second end region, the first end region of the flap connector being coupled to the projection portion of the first containment flap, the second end region of the flap connector being coupled to the projection portion of the second containment flap, and the middle portion of the flap connector being coupled to the central barrier region of the bodyside liner.

5. The absorbent article of claim 4, wherein the flap connector comprises a longitudinal length as measured in a direction parallel to the longitudinal axis of the absorbent article and the central barrier region comprises a longitudinal length as measured in the direction parallel to the longitudinal axis of the absorbent article, the longitudinal length of the flap connector being less than the longitudinal length of the central barrier region.

6. The absorbent article of claim 1, wherein the central barrier region comprises a longitudinal length as measured in a direction parallel to the longitudinal axis of the absorbent article, and the projection portion of the first containment flap and the projection portion of the second containment flap each have a lateral length as measured in a direction parallel to the lateral axis of the absorbent article, and wherein the longitudinal length of the central barrier region is greater than or equal to at least twice the lateral length of the first containment flap or the lateral length of the second containment flap.

7. The absorbent article of claim 1, wherein the central barrier region comprises a longitudinal length as measured in a direction parallel to the longitudinal axis of the absorbent article, and the longitudinal length of the central barrier region is between about 5.0 mm to about 150.0 mm.

8. The absorbent article of claim 1, wherein the absorbent article includes a front waist edge in the front waist region and a rear waist edge in the rear waist region, and wherein the central barrier region is located a distance from the front waist edge of between about ⅓ to about ⅔ of the length of the absorbent article.

9. The absorbent article of claim 1, wherein the bodyside liner further comprises a rear barrier region disposed in the rear waist region of the absorbent article, the rear barrier region being a rear portion of the bodyside liner not coupled to the absorbent body and comprising a first longitudinal side edge and a second longitudinal side edge, the first longitudinal side edge of the rear barrier region being coupled to the projection portion of the first containment flap and the second longitudinal side edge of the rear barrier region being coupled to the projection portion of the second containment flap such that when the absorbent article is in the relaxed configuration and the projection portion of the first containment flap and the projection portion of the second containment flap extend away from the absorbent body, the rear portion of the bodyside liner extends away from the absorbent body.

10. The absorbent article of claim 1, further comprising an acquisition layer, the acquisition layer being disposed between the absorbent body and the bodyside liner, the central portion of the bodyside liner not being coupled to the acquisition layer.

11. The absorbent article of claim 1, further comprising an acquisition layer, the acquisition layer being disposed between the absorbent body and the bodyside liner, the central portion of the bodyside liner being coupled to a central region of the acquisition layer, the central region of the acquisition layer not being coupled to the absorbent body.

12. An absorbent article including a front waist region, a rear waist region, a crotch region, a longitudinal axis and a lateral axis, the absorbent article comprising:
a chassis including a bodyside liner, an outer cover, and an absorbent body, the absorbent body disposed between the bodyside liner and the outer cover, the bodyside liner including a length that is at least 50% of a length of the absorbent article as measured in a direction parallel to the longitudinal axis; and
a pair of containment flaps comprising a first containment flap and a second containment flap, the first containment flap and the second containment flap each extending from the front waist region to the second waist region, the pair of containment flaps each comprising a base portion coupled to the chassis and a projection portion extending away from the absorbent body when the absorbent article is in a relaxed configuration;
wherein the bodyside liner comprises a barrier region, the barrier region being a portion of the bodyside liner configured to move independently from the absorbent body and to extend away from the absorbent body when the absorbent article is in the relaxed configuration.

13. The absorbent article of claim 12, wherein the barrier region comprises a first longitudinal side edge and a second longitudinal side edge, the first longitudinal side edge being coupled to the projection portion of the first containment flap and the second longitudinal side edge being coupled to the projection portion of the second containment flap.

14. The absorbent article of claim 13 wherein the first longitudinal side edge of the barrier region is coupled to the projection portion of the first containment flap adjacent a distal end of the projection portion of the first containment flap, and wherein the second longitudinal side edge of the central barrier region is coupled to the projection portion of the second containment flap adjacent a distal end of the projection portion of the second containment flap.

15. The absorbent article of claim 12, wherein the barrier region is disposed in the crotch region of the absorbent article.

16. The absorbent article of claim 12, further comprising:
a flap connector comprising a first end region, a middle portion, and a second end region, the first end region of the flap connector being coupled to the projection portion of the first containment flap, the second end region of the flap connector being coupled to the projection portion of the second containment flap, and the middle portion of the flap connector being coupled to the barrier region of the bodyside liner.

17. The absorbent article of claim 12, wherein the barrier region comprises a longitudinal length as measured in a direction parallel to the longitudinal axis of the absorbent article, and the projection portion of the first containment flap and the projection portion of the second containment flap each have a lateral length as measured a direction parallel to the lateral axis of the absorbent article, and wherein the longitudinal length of the barrier region is greater than or equal to at least twice the lateral length of the first containment flap or the lateral length of the second containment flap.

18. The absorbent article of claim 1, further comprising an acquisition layer, the acquisition layer being disposed between the absorbent body and the bodyside liner, the portion of the bodyside liner forming the barrier region not being coupled to the absorbent body and not being coupled to the acquisition layer.

19. An absorbent article including a front waist region, a rear waist region, a crotch region, a longitudinal axis and a lateral axis, the absorbent article comprising:
 a chassis including a bodyside liner, an outer cover, and an absorbent body, the absorbent body disposed between the bodyside liner and the outer cover;
 a pair of containment flaps comprising a first containment flap and a second containment flap, the first containment flap and the second containment flap each extending from the front waist region to the second waist region, the pair of containment flaps each comprising a base portion coupled to the chassis and a projection portion extending away from the absorbent body when the absorbent article is in a relaxed configuration; and
 a flap connector comprising a first end region, a middle portion, and a second end region; the first end region of the flap connector being coupled to the projection portion of the first containment flap, the second end region of the flap connector being coupled to the projection portion of the second containment flap;
 wherein the bodyside liner comprises a barrier region in the crotch region of the absorbent article, the barrier region being a portion of the bodyside liner not coupled to the absorbent body and comprising a first longitudinal side edge and a second longitudinal side edge, the barrier region being coupled to the middle portion of the flap connector;
 and wherein the flap connector and the barrier region are configured such that when the absorbent article is in the relaxed configuration and the projection portion of the first containment flap and the projection portion of the second containment flap extend away from the absorbent body, the flap connector and the portion of the bodyside liner not coupled to the absorbent body extend away from the absorbent body.

20. The absorbent article of claim 19, wherein the flap connector comprises a longitudinal length as measured in a direction parallel to the longitudinal axis of the absorbent article, the longitudinal length of the flap connector being between about 1.0 mm to about 10.0 mm.

* * * * *